US009750667B2

(12) United States Patent
Misner et al.

(10) Patent No.: US 9,750,667 B2
(45) Date of Patent: Sep. 5, 2017

(54) CLEANSING BAR

(71) Applicant: COLGATE-PALMOLIVE COMPANY, New York, NY (US)

(72) Inventors: Steve Misner, Verona, NJ (US); Long Pan, Cherry Hill, NJ (US); Diana Scala, Hillsborough, NJ (US); Regina Hourigan, Metuchen, NJ (US); Ravi Subramanyam, Belle Mead, NJ (US); Dennis Fletcher, Basking Ridge, NJ (US); Patricia Hall-Puzio, Succasunna, NJ (US); Shamim Ansari, Princeton, NJ (US); Derek Le, Champaign, IL (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 18 days.

(21) Appl. No.: 14/243,170

(22) Filed: Apr. 2, 2014

(65) Prior Publication Data
US 2014/0213497 A1   Jul. 31, 2014

Related U.S. Application Data

(63) Continuation of application No. 13/518,952, filed as application No. PCT/US2010/061703 on Dec. 22, 2010, now Pat. No. 8,729,137.

(60) Provisional application No. 61/289,430, filed on Dec. 23, 2009, provisional application No. 61/394,113, filed on Oct. 18, 2010.

(51) Int. Cl.
| *A61K 8/02* | (2006.01) |
| *C11D 3/12* | (2006.01) |
| *C11D 3/18* | (2006.01) |
| *C11D 3/382* | (2006.01) |
| *C11D 3/48* | (2006.01) |
| *C11D 17/00* | (2006.01) |
| *A61Q 19/10* | (2006.01) |
| *A61K 8/24* | (2006.01) |
| *A61K 8/25* | (2006.01) |

(52) U.S. Cl.
CPC ............. *A61K 8/0216* (2013.01); *A61K 8/24* (2013.01); *A61K 8/25* (2013.01); *A61Q 19/10* (2013.01); *C11D 3/126* (2013.01); *C11D 3/18* (2013.01); *C11D 3/382* (2013.01); *C11D 3/48* (2013.01); *C11D 17/006* (2013.01)

(58) Field of Classification Search
None
See application file for complete search history.

(56) References Cited

U.S. PATENT DOCUMENTS

| 3,804,654 A | 4/1974 | Liu |
| 4,666,624 A | 5/1987 | Irlam et al. |
| 4,678,593 A | 7/1987 | Ridley |
| 5,139,781 A | 8/1992 | Birtwistle et al. |
| 5,225,097 A | 7/1993 | Kacher et al. |
| 5,225,098 A | 7/1993 | Kacher et al. |
| 5,227,086 A | 7/1993 | Kacher et al. |
| 5,262,079 A | 11/1993 | Kacher et al. |
| 5,681,980 A | 10/1997 | Beerse et al. |
| 5,756,438 A * | 5/1998 | Rau ...................... A61K 8/0229 510/151 |
| 5,801,134 A | 9/1998 | Righton |
| 5,916,949 A | 6/1999 | Shapero et al. |
| 5,968,528 A | 10/1999 | Deckner et al. |
| 5,994,281 A * | 11/1999 | He ....................... C11D 17/006 510/141 |
| 6,114,291 A * | 9/2000 | He et al. ........................ 510/152 |
| 6,310,016 B1 * | 10/2001 | Behal et al. ................... 510/152 |
| 6,376,440 B1 | 4/2002 | Hennen et al. |
| 6,383,999 B1 | 5/2002 | Coyle et al. |
| 6,534,687 B2 | 3/2003 | Schultz et al. |
| 6,537,953 B2 | 3/2003 | Schultz et al. |
| 6,537,954 B2 | 3/2003 | Schultz et al. |
| 6,541,433 B2 | 4/2003 | Schultz et al. |
| 6,589,923 B2 | 7/2003 | Lenuck et al. |
| 6,949,493 B1 * | 9/2005 | Zhang et al. ................. 510/141 |
| 7,285,521 B2 | 10/2007 | Chakrabarty et al. |
| 7,442,674 B2 | 10/2008 | Polonka et al. |
| 7,446,081 B2 | 11/2008 | Tsaur et al. |
| 2001/0018068 A1 * | 8/2001 | Lorenzi et al. ............... 424/443 |
| 2002/0035048 A1 | 3/2002 | Schultz et al. |
| 2002/0037818 A1 | 3/2002 | Schultz et al. |
| 2002/0039978 A1 | 4/2002 | Schultz et al. |
| 2002/0042351 A1 | 4/2002 | Schultz et al. |
| 2002/0045555 A1 | 4/2002 | Andreas et al. |
| 2005/0187129 A1 | 8/2005 | Chakrabarty et al. |
| 2005/0220737 A1 | 10/2005 | Patel et al. |
| 2006/0111259 A1 | 5/2006 | Chakrabarty et al. |
| 2007/0042920 A1 * | 2/2007 | Schmit et al. ................. 510/130 |
| 2008/0125340 A1 | 5/2008 | Dail |
| 2008/0145664 A1 | 6/2008 | Sirovatka et al. |
| 2008/0153728 A1 | 6/2008 | Dail et al. |
| 2009/0286706 A1 * | 11/2009 | Chakrabarty et al. ........ 510/131 |

FOREIGN PATENT DOCUMENTS

| DE | 19708605 | 9/1998 |
| DE | 19923076 | 11/2000 |

(Continued)

OTHER PUBLICATIONS

Carretero et al., "Clay and non-clay minerals in teh pharmaceutical and cosmetic industries Part II. Active ingredients," Applied Clay Science, 2010, 47:171-181.

(Continued)

*Primary Examiner* — Bethany Barham
*Assistant Examiner* — Ping Cao

(57) ABSTRACT

A cleansing bar comprising at least one member chosen from clay and talc, wherein a total amount of clay and talc is present in an amount that is greater than any other material in the cleansing bar, at least one cleanser chosen from soap and surfactant, and a binder present in an amount to structure the cleansing bar into a bar.

15 Claims, 2 Drawing Sheets

(56) References Cited

FOREIGN PATENT DOCUMENTS

| EP | 0210842 | | 2/1987 | | |
|---|---|---|---|---|---|
| EP | 0312278 | * | 11/1988 | ............. | C11D 17/00 |
| EP | 1141216 | | 10/2001 | | |
| GB | 2060676 | | 5/1981 | | |
| GB | 2083490 | | 3/1982 | | |
| GB | 2083491 | | 3/1982 | | |
| GB | 2127426 | | 4/1984 | | |
| GB | 2317396 | | 3/1998 | | |
| JP | 7-258697 A | | 10/1995 | | |
| JP | 9-087687 A | | 3/1997 | | |
| WO | WO 97/22684 | | 6/1997 | | |
| WO | WO00/42159 | * | 7/2000 | ............. | C11D 17/00 |
| WO | WO 02/46346 | | 6/2002 | | |
| WO | WO 2006/094586 | | 9/2006 | | |
| WO | WO 2006/097238 | | 9/2006 | | |
| WO | WO 2010/057850 | | 5/2010 | | |

OTHER PUBLICATIONS

Galindo et al., "Compositional, technical and safety specifications of clays to be used as pharmaceutical and cosmetic products," Applied Clay Science, 2007, 36:51-63.
International Search Report and Written Opinion in International Application No. PCT/US10/061703, mailed Apr. 20, 2011.
Ka Min Performance Materials, 2008, Polygloss® 90 Specialty Kaolin Technical Data Sheet, Revised Jan. 1, 2009.
Written Opinion in International Application No. PCT/US10/061703, mailed Dec. 18, 2011.

* cited by examiner

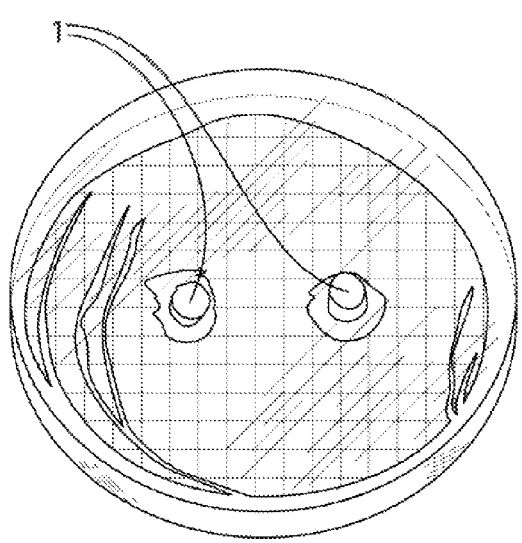
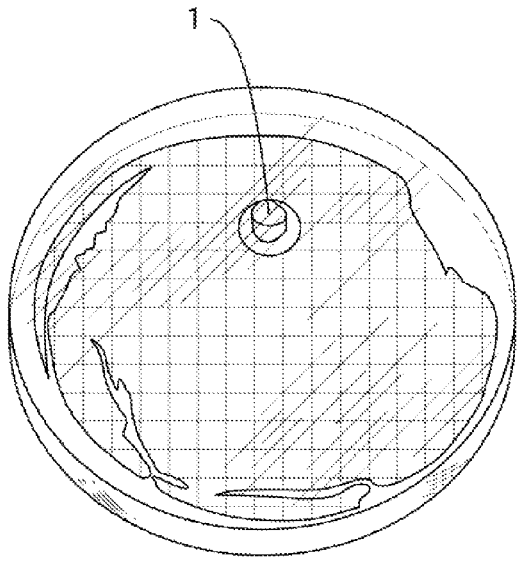
FIG. 1A  FIG. 1B
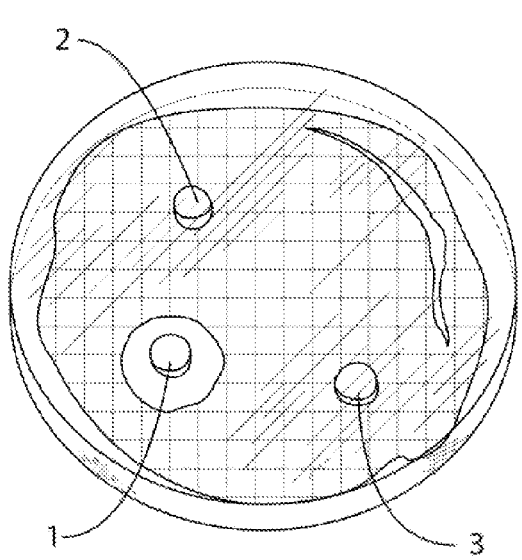
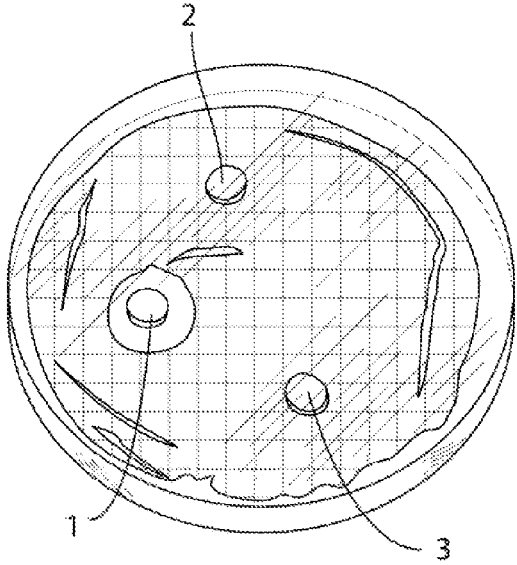
FIG. 1C  FIG. 1D

CLEANSING BAR

CROSS REFERENCE TO RELATED APPLICATIONS

This application is a continuation of application Ser. No. 13/518,952, with a national stage entry date on 25 Jun. 2012, which is a national stage entry under 35 U.S.C. §371 of International Patent Application No. PCT/US2010/061703, filed on 22 Dec. 2010, which claims priority to U.S. Provisional Patent Application Nos. 61/289,430, filed 23 Dec. 2009, and 61/394,113, filed 18 Oct. 2010, all of which are incorporated herein by reference.

BACKGROUND

Cleansing bars have historically been made from salts of fatty acids (soaps). They can also be made from surfactants (syndet bars), or they can be made from a combination of soaps and surfactants (combars). Typically, the soaps and/or surfactants have been the dominate ingredient in cleansing bars.

As the cost of raw materials increases, such as oil, the cost of soaps and surfactants increase. With increasing costs, the profitability of cleansing bars decreases. It would be desirable to replace the high cost materials with lower cost materials and still deliver a desired level of cleaning and lathering.

Attempts have been made to use clay and talc in bars, but just adding in talc and/or clay does not result in acceptable bars. For example, see Table 1 in WO2006/094586A1 in which talc and/or clay were used to make bars. The bars made from these compositions had no structural integrity or were too brittle.

While it would be desirable to use clay and/or talc in the manufacture of a cleansing bar, additional design is needed to develop a bar with commercially desirable properties for structural integrity, lathering, cracking, texture, and use-up rate.

SUMMARY

A cleansing bar comprising at least one member chosen from clay and talc, wherein a total amount of clay and talc is present in an amount that is greater than any other material in the cleansing bar, at least one cleanser chosen from soap and surfactant, and a binder present in an amount to structure the cleansing bar into a bar.

Also, a method of making the cleansing bar comprising mixing the clay and/or talc with the binder before mixing in the cleansing agent.

Also, a method of removing bacteria from skin comprising washing skin with the cleansing bar.

Also, a method of inhibiting bacterial growth on skin comprising washing skin with the cleansing bar.

BRIEF DESCRIPTION OF FIGURES

FIG. 1A demonstrates the results obtained from a clay bar assayed alone using zone of inhibition test.

FIG. 1B demonstrates the results obtained from a clay bar assayed with a plain 85/15 bar soap using the zone of inhibition test.

FIGS. 1C and 1D demonstrate repeated Zone of Inhibition testing against other products.

DETAILED DESCRIPTION

Figure 2A:
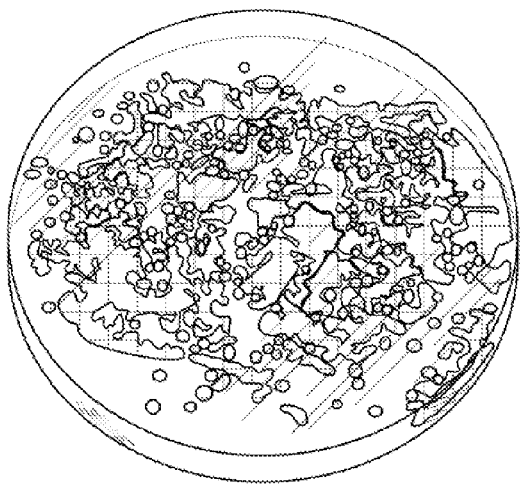
FIGS. 2A-2C demonstrate Rapid Agar Plate Assessment (RAPA) results obtained from the following: clay bar, Lever2000™, and Irish Spring™.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight of the entire composition. The amounts given are based on the active weight of the material.

The composition is a cleansing bar. The cleanser can be soap, a surfactant, or a combination of soap and surfactant. The bar can be used for personal cleansing or as a laundry bar.

The composition includes clay and/or talc. In certain embodiments, the amount of clay and/or talc is greater than an amount of any other material in the composition. In certain embodiments, this refers to the total amount of clay and talc (at least one of which is present) being greater than any one specific material. For example, if the cleansing bar contains more than one soap/surfactant, the amount of clay/talc is greater than an amount of either soap/surfactant. In other embodiments, the total amount of clay/talc is greater than the total amounts of material in any given class of materials. For example, if there are two soaps/surfactants in the cleansing bar, the amount of clay/talc is greater than the combined amounts of these two soaps/surfactants. In certain embodiments, the amount of clay/talc is at least 40 weight % of the cleansing bar. In other embodiments, the amount of clay/talc is at least 45, 50, 51, 52, 53, 54, 55, 56, 57, 58, 59, 60, 61, 62, 63, 64, or 65 weight %. In other embodiments, the amount of clay/talc is 50 to 65 weight %. The preceding ranges apply to clay alone, talc alone, or a combination of clay and talc. In certain embodiments, the composition includes clay and talc.

In certain embodiments, clay is present and the amount of talc is 8 to 20 weight %. In other embodiments, the weight ratio of clay to talc is 12:1 to 4:1. In other embodiments, the ratio is 6:1, 5:1, or 4:1.

The clay can be any type of clay. Examples of clays include, but are not limited to, kaolin, kaolinite, dickite, halloysite, nacrite, smectite, montmorillonite, nontronite, illite, bentonite, attapulgite, palygorskite, sepiolite, hormite, pyrophyllite, chlorite, and aluminosilicates. In one embodiment, the clay is kaolin. In another embodiment, the clay is smectite. In another embodiment, the clay is bentonite.

Sources for clay include, but are not limited to, i) National Standard 325 Mesh, National Premium WT, National Premium 325 Mesh WT, and National Premium 325 Mesh from Bentonite Performance Minerals. LLC; ii) KaMin™ 90, KaMin™ 90B, and Polygloss™ 90 from KaMin™ Performance Minerals; iii) EPK kaolin from Feldspar Corp./Imerys National Ceramics; iv) Electros kaolin, SIM 90 kaolin USP, Lion Kaolin USP, and Plus White kaolin from Charles B. Chrystal Co., Inc.; v) Big Horn CH 200 from Wyo-Ben; vi) SCP bentonite H and SCP bentonite L from Southern Clay Products, Inc.; vii) ASP 170, ASP G90, and ASP G92 from Kaolin BASF; and viii) Bentonite 1, Bentonite 2, Inorganic Gelatin 1, and Inorganic Gelatine 2 from Wufu Feishang Non-metallic Minerals.

In one embodiment, the clay can be modeling clay, which is a mixture of clay, glue, and other materials. An example of modeling clay is Magic Mud™ from K-Play Co. of Great Barrington, Mass. Another example of a modeling clay can be found in U.S. Pat. No. 3,804,654. This modeling clay is a mixture of 20-50 weight % clay, 13-45 weight % talc, 20-25 weight % glue, 6.5-8 weight % water, 0.5-1.5 weight % hydrocarbon petroleum distillate oil, 0.5-1.5 weight % waxy paraffinic hydrocarbon oil, 1.5-2 weight % aluminum sulfate, 0.9-1.3 weight % glycerin, and 0.4-0.9 weight % dimethyl polysiloxane.

The binder can be any material that binds clay and/or talc. The binder can be present in any amount that will bind the clay/talc. In one embodiment, the amount of binder is 1 to 15 weight % of the composition. In other embodiments, the amount of binder is at least 1, 2, 3, 4, 5, 6, 7, 8, 9, or 10 up to 15 weight % or less than 14, 13, 12, 11, 10, 9, 8, 7, 6, 5, 4, 3, or 2 down to 1 weight %. In another embodiment, the amount of binder is at least 10 weight %.

Examples of the binder include, but are not limited to, adhesive, glue, wax, fatty acid, fatty alcohol, silicone grease (such as GRS-9623-30 from NuSil Technologies), Magi-Glue™ biopolymer adhesive from Athena Environmental Sciences, AQ38S or AQ55S sulfopolyesters from Eastman, and, polyvinyl alcohol polymer (such as Celvol™ 205 from Celanese).

To increase the stability of the cleansing bars, water insoluble binders can be selected. One type of water insoluble binder is wax. When formulated with water insoluble binders, the cleansing bar is resistant to wet environments. When formulated with wax, cleansing bars can last a day without any significant disintegration.

Examples of waxes include, but are not limited hydrogenated oils, petroleum waxes, paraffin, hydrogenated soybean oil, castor wax, ceresine, ozokerite, carnauba, bees wax, candelilla, polymethylene wax, polyethylene wax, and microcrystalline wax. In one embodiment, the hydrogenated oil is hydrogenated soybean oil. In one embodiment, the hydrogenated soybean oil is almost, but not fully hydrogenated. The amount of hydrogenation is measured by the iodine value. The iodine value can be measured by ASTM D5554-95 (2006). In one embodiment, the iodine value of the hydrogenated soybean oil used herein is greater than 0 to 20. In one embodiment, the iodine value is 1 to 5. In another embodiment, the soybean oil is fully hydrogenated with an iodine value of 0. In another embodiment, the iodine value is up to 20. In one embodiment, the amount of hydrogenated soybean oil is 4 to 5 weight %.

Fatty material refers to a fatty acid/alcohol with a $C_8$-$C_{22}$ unbranched aliphatic tail (chain), which is either saturated or unsaturated. The hydrophobic property of the fatty material is used to improve dispersibility.

Types of fatty material include, but are not limited to, oils, fatty acids in acid form, and fatty alcohols. Examples of fatty material include, but are not limited to, palm kernel oil, stearyl alcohol, and behenyl alcohol. The amount of fatty material can be any desired amount. Generally, the amount is less than 8 weight % to minimize the effect of reducing lather. In certain embodiments, the amount of fatty material is 0.01 to 8 weight %. While residual tatty acids can be present in soap bars, the amount of fatty acid herein is an amount that provides structure to form a soap bar.

In certain embodiments, the binder comprises the hydrogenated soybean oil, in particular the 1-5 iodine value hydrogenated soybean oil, and the fatty material comprises palm kernel oil. This combination will make the cleansing bar more plastic to reduce or eliminate cracking and to reduce the slough from the bar.

The term cleansing agent refers to soap and/or surfactant. It is used to refer to soap alone, surfactant alone, or a combination of soap and surfactant. The amount of cleansing agent in the cleansing bar is 5 to 30 weight %. In other embodiments, the amount of cleansing agent is 10 to 30 weigh/t % or 10 to 20 weight %. In certain embodiments, surfactants are present in an amount that is greater than an amount of soap. In other embodiments, the amount of soap is less than 5, 4, 3, 2, 1, 0.5, or 0.1 weight %, or soap is not present.

Soap refers to the salts of fatty acids that are typically used to make soap bars. Soap can be a blend of 65-85 weight % $C_{16}$-$C_{18}$ and 15-35 weight % $C_{12}$-$C_{14}$ fatty acids based on the total weight of the soap. In one embodiment, the blend is 80/20. As used throughout, a reference to 80/20 soap refers to this blend. The $C_{16}$-$C_{18}$ can be obtained from tallow, and the $C_{12}$-$C_{14}$ can be obtained from lauric, palm kernel, or coconut oils. A typical 80/20 soap contains 68.8 weight % sodium soap, 30 weight % water, 0.5 weight % glycerin, 0.5 weight % sodium chloride, and 0.2 weight % sodium hydroxide.

The soap chips useful herein for the purpose of this invention also include but are not limited to the well known alkali metal salts of aliphatic (alkanoic or alkenoic) acids having about as 8 to 22 carbon atoms alkyl, preferably 10 to 20 carbon atoms alkyl chain. These may be described as alkali metal carboxylates of acrylic hydrocarbons having about 12 to about 22 carbon atoms. Any other surfactant can also be present in the soap chip such as those mentioned in U.S. Pat. No. 5,139,781 at column 5, line 35 to column 11, line 46. In certain embodiments, the amount of soap is 8 to 20 weight %.

Surfactant refers to any anionic, nonionic, cationic, amphoteric, or zwitterionic surfactant. The total amount of surfactant can be any desired amount. In certain embodiments, the amount of surfactant in the cleansing bar is 5 to 25 weight %, 8 to 25 weight %, 10 to 25 weight %, 10 to 20 weight %, 5 to 15 weight %, or 10 to 15 weight %. Examples of anionic surfactant include, but are not limited to, alkyl ($C_6$-$C_{22}$) materials such as alkyl sulfates, alkyl sulfonates, alkyl benzene sulfonates, lauryl sulfates, lauryl ether sulfates, alkyl phosphates, alkyl ether sulfates, alkyl alpha olefin sulfonates, alkyl taurates, alkyl isethionates (SCI), alkyl glyceryl ether sulfonates (AGES), sulfosuccinates and the like. These anionic surfactants can be alkoxylated, for example, ethoxylated, although alkoxylation is not required. These surfactants are typically highly water soluble as their sodium, potassium, alkyl and ammonium or alkanol ammonium containing salt form and can provide high foaming cleansing power. In certain embodiments, examples of anionic surfactants include, but are not limited to, sodium lauryl ether (laureth) sulfate (average of 2 to 15 EO per mole, such as 2, 3, 4, or 5) sodium cocoyl isethionate, and sodium cocoyl methyl isethionate. For laundry, examples of anionic surfactants include, but are not limited to, alkyl sulfates, such as sodium lauryl sulfate, ammonium alkyl sulfate salts, alkyl ethoxylate sulfates, alkylbenzene sulfonates, such as dodecylbenzene sulfonate, nonionic surfactants, polyethoxylated alcohols, such as C12-C13 alcohol with an average of 6.5 ethoxyl units, polyhydroxy fatty acid amides, such as C12-C13 amide with N-linked methyl or N-linked reduced sugar. Anionic surfactants can be included in any desired amount. In one embodiment, anionic surfactants are present in the amounts given above for surfactants.

Examples of zwitterionic/amphoteric surfactants include, but are not limited to, derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to, a range of betaines including, for example, high alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups such as the cocamidopropyl and cocoamidoethyl betaines. In one embodiment, the zwitterionic surfactant comprises cocamidopropyl betaine. Zwitterionic/amphoteric surfactants can be included in any desired amount. In one embodiment, zwitterionic/amphoteric surfactants are present in the amounts given above for surfactants.

Examples of nonionic surfactants include, but are not limited to, ethoxylated fatty alcohols (such as the steareth-2 to steareth-100 series from Croda Chemicals, Inc. sold under the trademark Brij, such as steareth-2, steareth-4, steareth-10, steareth-20, or steareth-100), polysorbate 20, long chain alkyl glucosides having $C_8$-$C_{22}$ alkyl groups; coconut fatty acid monoethanolamides such as cocamide MEA; coconut fatty acid diethanolamides, fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols): polypropylene glycol ethoxylates (for example the Pluronic™ block copolymers commercially available from BASF); fatty acid alkylolamides, (fatty acid amide polyethylene glycols); N-alkyl-, N-alkoxypolyhydroxy fatty acid amides: sucrose esters; sorbitol esters; polyglycol ethers; and combinations thereof. Nonionic surfactants can be included in any desired amount. In one embodiment, nonionic surfactants are present in the amounts given above for surfactants.

The cleansing bars can contain water. In certain embodiments, the amount of water is greater than 0 up to 20 weight %, up to 15 weight %, up to 10 weight %, 5 to 20 weight %, or 5 to 15 weight %, 10 to 20 weight %, or 10 to 15 weight %.

Optionally, the cleansing bar can contain foam boosters. Examples of foam boosters include, but are not limited to, certain amphoteric surfactants, cocomonoethanolamide (CMEA), cocoamidopropylamine oxide, cetyl dimethylamine chloride, decylamine oxide, lauryl/myristyl amidopropryl amine oxide, lauramine oxide, alkyldimethyl amine n-oxide, and myristamine oxide. in certain embodiments, the amount of foam booster is 2 to 10 weight %.

Optionally, the cleansing bar can contain any additional materials that are added to personal cleansing or laundry bars. Examples include, but are not limited to, coloring agent, dye, pigment, fragrance, preservative, biocide, antibacterial agent, exfoliating/scrubbing particles, and filler.

The bars can be made by traditional manufacturing methods. First, meltable ingredients are added to a mixer and melted at 60 to 80° C. (70° C., 160° F.). This temperature is maintained throughout manufacturing. Next, talc and other non-soluble solid additives are mixed into the melted ingredients. Next, clay is mixed in. Liquid surfactants, water, and other room temperature liquids are added and mixed in. The composition is removed from the mixer and milled 2 to 3 times to complete the mixing.

The materials are selected in combination to achieve a bar having desired levels for hardness, texture, lather, use-up, and/or sloughing. The bar can be designed to have parity or improved properties as compared to current bars.

The bars are tested for lather by a hand washing test. Panelists are instructed to pass the bar 5 times on the hands in 35-37° C. tap water. The amount of lather generated by the prototypes is compared to the lather produced by a standard of Irish Spring™ Aloe bar soap from Colgate-Palmolive Company.

Dispersibility is designed to measure the rate at which bar soaps disintegrate in water. Although consumers typically would not leave their soap products completely submerged in water, this test gives a convenient means to qualitatively measure how well the bar holds together in a humid environment. One gram of the sample is placed in a scintillation vial with 9 g of tap water. The vial is left untouched, and the amount of material dispersed is determined by looking at how much of the soap is left at specific time intervals. The prototype samples are tested in parallel with a standard Palmolive™ brand soap. For the samples that had high water uptake, their increase in size was directly attributed to the amount of soap dispersed.

The dry bar is initially weighed. Then the bar is rolled in the operator's hand for 10 sec in the presence of a gentle stream of 38° C. tap water. To insure consistency, washing is performed using one operator. The washings are repeated for a total of three washes per day, for a three day period. Each ten second wash is separated by a 3 hour interval. The bars are kept in soap dishes with drainage, to prevent slough (wet mush) from forming. After each wash is completed, the bars are allowed to dry in the soap dishes, and the post-wash mass is recorded. The use up rate is then obtained by subtracting the difference in weights and plotting against the number of washes. The use up rates for the bars is compared against that of Irish Spring Aloe bar soap.

Moisturization studies are done in vitro using the pigskin wash method. The pigskin samples are from Animal Technologies, Inc. Control and Prototype samples are prepared in 5 wt %/volume solutions in tap water. DI water washed and defatted full-thickness pigskin is placed on a 12-cell sample stage. Each circular cell has a 2 cm diameter, and the dermis side of the pigskin is used. After wetting with 250 μL of tap water, 100 μL of the prepared washing solution is lathered on the sample cell area of the pigskin for 30 s. The lather is rinsed off 10 times with 250 μL of tap water. The pigskin is then allowed to air-dry in an environment controlled room (23.9° C. (75° F.)/40% RH) overnight (about 24 hrs). TEWL measurements are taken with a DermaLab TEWL Meter (Dermalab, FL). Higher conductivity translates to higher water content, thus higher moisturization.

In bars that contain clay and talc, the bar feels more smooth as compared to a bar with clay alone. Also, the combination reduces the amount of residue.

Specific Embodiments of the Invention

The invention is further described in the following examples. The examples are merely illustrative and do not in any way limit the scope of the invention as described and claimed. In the examples below, the listed weight is based on the as supplied weight of the material along with the % active.

The following tests are used for evaluation.

Slough is calculated as the % weight loss of a soap bar after soaking in room temperature (about 23° C.) water for about 17 hours.

Slough ratio is calculated as the slough of a test bar divided by the slough of a reference 85/15 bar. This compares how close the slough of a test bar is to a typical soap bar. The composition of a typical 85/15 bar is given below.

Use up is measured by holding a bar for 10 seconds in 38° C. tap water while rotating the bar. It is returned to a soap dish with drainage holes to prevent slough from forming. It is washed a total of 20 times with 10 washes per day with 30 minutes between washes. After the last wash, it is allowed to dry overnight at room temperature (about 23° C.) in a dry soap dish. Use up is expressed as percent weight loss.

Use up ratio is calculated as the use up percentage of a test bar divided by the use up of a reference 85/15 bar. This compares how close the use up of a test bar is to a typical soap bar.

A typical 85/15 soap bar is about 78.5 weight % sodium soap, about 15.5 weight % water, about 3.25 weight % glycerin, about 1 weight % sodium chloride, and minor amounts of color, fragrance, and unreacted reactants and byproducts of the soap making process. The 85/15 refers to the weight percentage of the total fatty acids in the soap. The fatty acids are typically i) 85 weight % tallow fatty acids and 15 weight % coconut fatty acids, ii) 85 weight % tallow fatty acids and 15 weight % palm kernel fatty acids, or iii) 92.5 weight % tallow fatty acid and 7.5 weight % lauric acid. Each of these soaps will have a similar slough and use up. They are used interchangeably as comparative examples below.

The following materials are used in the following examples.

Clays

| | | |
|---|---|---|
| Bentonite Performance Minerals, LLC | National Standard 325 Mesh | bentonite |
| Bentonite Performance Minerals, LLC | National Premium WT | bentonite |
| Bentonite Performance Minerals, LLC | National Premium 325 Mesh WT | bentonite |
| Bentonite Performance Minerals, LLC | National Premium 325 Mesh | bentonite |
| KaMin Performance Minerals | KaMin ™ 90 | kaolin |
| KaMin Performance Minerals | KaMin ™ 90B | kaolin |
| KaMin Performance Minerals | Polygloss ™ 90 | kaolin |
| Feldspar Corp./Imerys National Ceramics | EPK Kaolin | kaolin |
| Charles B. Chrystal Co., Inc | Electros Kaolin | kaolin |
| Charles B. Chrystal Co., Inc. | SIM 90 Kaolin USP | kaolin |
| Charles B. Chrystal Co., Inc. | Lion Kaolin USP | kaolin |
| Charles B. Chrystal Co., Inc. | Pure White Kaolin | kaolin |
| Wyo-Ben | Big Horn CH 200 | bentonite |
| Southern Clay Products, Inc. | SCP Bentonite H | bentonite |
| Southern Clay Products, Inc. | SCP Bentonite L | bentonite |
| Kaolin BASF | ASP 170 Kaolin clay | kaolin |
| Kaolin BASF | ASP G90 Kaolin clay | kaolin |
| Kaolin BASF | ASP G92 Kaolin clay | kaolin |
| Imerys Performance Minerals | Rogers | kaolin |
| Imerys Performance Minerals | Supreme | kaolin |
| Imerys Performance Minerals | Allen G | kaolin |
| Wufu Feishang Non-metallic Materials | Bentonite 1 | bentonite |
| Wufu Feishang Non-metallic Materials | Bentonite 2 | bentonite |
| Wufu Feishang Non-metallic Materials | Inorganic Gelatin 1 | bentonite |
| Wufu Feishang Non-metallic Materials | Inorganic Gelatin 2 | bentonite |
| American Art Clay Co. | Magic Mud ™ | modeling clay |

Adhesives

| | | |
|---|---|---|
| NuSil Technologies | GRS-9623-30 | Silicone Grease |
| Athena Environmental Sciences | MagiGlue ™ Natural, | Biopolymer Adhesive |
| Eastman | AQ 38S | Sulfopolyester |
| Eastman | AQ 55S | Sulfopolyester |
| Celanese | Celvol ™ 205 | Polyvinyl alcohol (PVOH) polymer |

Surfactants/Emulsifiers

| | | |
|---|---|---|
| Stepan Co. | Nacconal 90G | Dodecyl benzene sulfonate (DDBS) |
| Cognis | Cocoamidopropyl Betaine | (CAPB) |
| Cognis | Cocomonoethanolamide | (CMEA) |
| Albright & Wilson | Sodium Lauryl Sulfate Powdered (SLS) | |
| Croda Chemicals, Inc. | BRIJ-72 ™ | (Steareth-2) |
| Croda Chemicals, Inc. | BRIJ-78 ™ | (Steareth-20) |

Miscellaneous Ingredients

| | |
|---|---|
| JT Baker | Sodium Sulfate ($Na_2SO_4$) |
| Cognis | Glycerin |
| Dow Chemical Co. | PEG 600 |
| Penreco Peneteck Lt. | Mineral Oil |
| Strahl & Pitsch, Inc. | Beeswax |
| Strahl & Pitsch, Inc. | Ceresine Wax |
| FMC Biopolymer | Carrageenan Gum |
| Cargill Co. | Coconut Oil |
| Acme Hardesty | Palmitic Acid |
| Dow Chemical Co. | POLYOX ™ WSR-N 750 PEG-7M |

The following procedures are used to make the bars.

Prototype Clay Bar Soaps from Commercial Modeling Clay. Initial prototype clay bars were prepared from commercially available modeling clays to test the viability of the proposed invention. The procedure is as follows:

1. Mill clay 2× to soften and form smaller particles for more efficient incorporation of ingredients.
2. Add formula amount of Talc and $Na_2SO_4$.
3. Add formula amount of glycerin.

4. Add formula amount of SLES.
5. Blend formula ingredients together with spatula until mix is visually uniform.
6. Mill the formula mix 2× to homogenize ingredients and produce a more pliable/uniform blend.
7. Add formula amount of fragrance, blending manually with spatula until batch is visually uniform.
8. Mill batch 2× to fully incorporate the fragrance.
9. Manually form five ~110 gram bars.
10. Wrap bars in paper towels and maintain for 24 hours to allow further hardening before washing.

Polyvinyl Alcohol (Celvol™ 205) and Sulfopolyesters (AQ Polymers) Preparation
1. Add formula amount of dry polymer to formula amount of DI water.
2. Heat solution to approximately 70-80° C. using a hot plate and mix solution using stir bar until solution is homogenous (no solid polymer visible).
3. Deliver required amount to clay mixture.

Kaolin clay with adhesives.
1. Weigh out formula amount of clay into a mortar.
2. Add formula amount of Na$_2$SO$_4$ to mortar with clay and mix well (per sample formulation).
3. Add formula amount of adhesive to the mortar with the clay. (NOTE: For the PVOH and sulfopolyesters, this means adding the formula amount of the prepared liquid adhesive solution.
4. Add formula amount of DI water to mortar (NOTE: This only pertains to the MagiGlue™ based samples).
5. Thoroughly blend the mixture in the mortar using the pestle until it is homogenous.
6. Mold the dough-like mixture into miniature bar shape by hand.
7. Allow prepared samples to dry for 24 hours before analysis.

Kaolin Clay Soap from Kaolin/Adhesive/Surfactants
1. Add clay, powder surfactants (SLS, CMEA, DDBS), Polyox™, and/or MagiGlue™ according to formula together in a large (4-liter size minimum) container.
2. Mix the powders together thoroughly by shaking the container rigorously to form a vortex (as to imitate an industrial powder mixer) for approximately 3-5 minutes to form the dry blend.
3. Prepare AQ 38S adhesive solution from above.
4. Mix (with overhead stirrer) glycerin with either DI water (for MagiGlue™ based samples) or with adhesive solution (for AQ 38S based samples) in formula prescribed ratios to form liquid blend.
5. Add formula amount of CAPB to the liquid blend and mix thoroughly using an overhead stirrer.
6. Add formula amount of dry blend to a large mixing container and slowly pour liquid blend into dry blend while mixing with overhead stirrer.
7. Once dough-like composition is formed, run the mixture through the 3-roll mill at least 5-7 times or until homogenous.
8. Press the mixture into a bar soap shape using soap press.
9. Leave samples uncovered in flame hood to dry at room temperature over the course of 1 week.

When the clay and liquid were mixed, the resulting mixture resembled a doughy mixture similar to that of when flour is mixed with water. Since it is desired to avoid unnecessary water added to the product, the least amount of water necessary to facilitate the dispersion of the adhesive and liquid components of the formulation into the clay was used. This created a difficult mixture to thoroughly homogenize with bench-top equipment. Thus, a bench-top 3-roll mill was used.

Batch Information for Preliminary Adhesive Screening Samples

| | Sample | | | | |
|---|---|---|---|---|---|
| Ingredient | 1 wt. % | 2 wt. % | 3 wt. % | 4 wt. % | 5 wt. % |
| Electros Kaolin | 70 | 70 | 70 | 70 | 70 |
| DI Water | 20 | 25 | 25 | 25 | 0 |
| MagiGlue ™ | 10 | 0 | 0 | 0 | 0 |
| AQ 38S | 0 | 5 | 0 | 0 | 0 |
| AQ 55S | 0 | 0 | 5 | 0 | 0 |
| Celvol ™ 205 | 0 | 0 | 0 | 5 | 0 |
| GRS-9623-30 | 0 | 0 | 0 | 0 | 30 |
| Total | 100 | 100 | 100 | 100 | 100 |

Batch Information for Adhesive Concentration Study Samples

| | Sample | | | | | |
|---|---|---|---|---|---|---|
| | 6 wt. % | 7 wt. % | 8 wt. % | 9 wt. % | 10 wt. % | 11 wt. % |
| Electros Kaolin | 75 | 75 | 75 | 75 | 75 | 75 |
| DI Water | 22.5 | 12.5 | 24 | 20 | 24 | 20 |
| MagiGlue ™ | 2.5 | 12.5 | 0 | 0 | 0 | 0 |
| AQ 38S | 0 | 0 | 1 | 5 | 0 | 0 |
| Celvol ™ 205 | 0 | 0 | 0 | 0 | 1 | 5 |
| Total | 100 | 100 | 100 | 100 | 100 | 100 |

Batch Information for Kaolin Based Clay Soap Prototypes

| | Sample # | | |
|---|---|---|---|
| | 12 wt. % | 13 wt. % | 14 wt. % |
| Polygloss ™ 90 | 65 | 60 | 60 |
| Nacconol ™ 90G (dodecyl benzene sulfonate, DDBS) | 2.53 | 2.85 | 2.85 |
| Cocoamidopropyl Betaine (CAPB) | 0.67 | 0.75 | 0.75 |
| Cocomonoethanolamide (CMEA) | 3.1 | 3.6 | 3.6 |
| SLS Powder | 3.2 | 7.3 | 7.3 |
| POLYOX ™ WSR-N 750 | 0.5 | 0.5 | 0.5 |
| Glycerin | 5 | 5 | 5 |
| MagiGlue ™ | 0 | 0 | 5 |
| Eastman AQ 38S | 3 | 3 | 0 |
| DI Water | 17 | 17 | 15 |
| Total | 100 | 100 | 100 |

Batch Information for Addition of Wax and/or Fatty Acids Samples

| | Sample | | |
|---|---|---|---|
| Ingredient | 15 wt. % | 16 wt. % | 17 wt. % |
| Polygloss ™ 90 | 65 | 65 | 55 |
| SLS | 10 | 10 | 12 |
| Glycerin | 3 | 0 | 3 |
| DI Water | 2.5 | 2.5 | 12 |
| AQ38S | 12 | 15 | 3 |
| Beeswax | 5 | 5 | 4.05 |

-continued

| Ingredient | Sample 15 wt. % | Sample 16 wt. % | Sample 17 wt. % |
|---|---|---|---|
| Coconut Oil | 0 | 0 | 4.13 |
| Palmitic Acid | 0 | 0. | 4.12 |
| Steareth-2 | 1.7 | 1.7 | 1.8 |
| Steareth-20 | 0.8 | 0.8 | 0.9 |
| Total | 100 | 100 | 100 |

Batch Information for Utilization of PVOH in Formulation

| Ingredient | Sample 18 wt. % | Sample 19 wt. % |
|---|---|---|
| Polygloss ™ 90 | 60 | 60 |
| SLS | 10.75 | 11.25 |
| Glycerin | 3 | 3 |
| NaSO4 | 1.25 | 0.75 |
| AQ38S | 0 | 3.75 |
| Celvol ™ 205 | 6.25 | 2.5 |
| DI Water | 18.75 | 18.75 |
| Total | 100 | 100 |

Batch information for Utilization of Alternate Humectants in Formulation

| Ingredient | Sample 20 wt. % | Sample 21 wt. % | Sample 22 wt. % |
|---|---|---|---|
| Polygloss ™ 90 | 60 | 60 | 60 |
| SLS | 10.75 | 10.75 | 10.75 |
| NaSO4 | 1.25 | 1.25 | 1.25 |
| Celvol ™ 205 | 7 | 6.25 | 6.25 |
| DI Water | 21 | 18.75 | 18.75 |
| Mineral Oil | 0 | 3 | 0 |
| PEG 600 | 0 | 0 | 3 |
| Total | 100 | 20 | 100 |

Initial prototype clay bar soaps were created from commercially available modeling clays. Modeling clay contains about 50% clay in addition to wax and plasticizing agents. Since these latter ingredients are not needed for bar soap formulations, most of our formulations were prepared using pure clay. The following observations were noted during the preparation of modeling clay soap samples.

Commercially purchased modeling clay was used without modification to make prototype bars PI-PXVIII, however, due to the clay's high moisture level (e.g. 20%-22%), the resulting bars were very sticky and soft. The calculated moisture level in these first bars ranged from 16%-18%, which was well above the traditional bar soap moisture levels of 10%-12%. Several days of drying were required before these prototype bars could be evaluated.

Successive formulations, Prototypes PXIX-PXXI, were produced from pre-dried modeling clay. When this powdered clay was combined with glycerin, talc, surfactant and Polyox™, the resulting bar hardness was comparable to typical bar soaps having 10%-12% moisture levels.

Multiple millings of the combined raw materials (amalgamator mix) helped to plasticize the soap mass.

Additional millings (2-3) after addition of fragrance resulted in a more refined soap texture and produced a very formable mass for pressing into bar shapes.

The density of the modeling clay prototypes was much higher than conventional bar soaps, e.g.: a 100 g bar was ~70% of the size of an equal weight sodium soap bar. Because Prototypes XI-XVI contained 5%-20% soap (80Tallow/20Palm Kernel Oil base), they were less dense.

Processability of the lower moisture content prototypes, Prototypes XXII and XV (8%-10% moisture) were comparable to conventional bar soaps.

Prototypes XXIII and XXIV with 20% SLES were significantly stickier than the prototypes having 17.5% SLES. Processability was more difficult, the lather profile was not as good, and the skin felt tacky after the wash.

Prototypes XXII and XXV exhibited the best processing and aesthetic properties.

These prototypes will be the basis for the next round of development work. Prototypes PI-PXI were evaluated for their lather, texture, and use-up rates in comparison with Irish Spring™ Aloe bar soap. PXII-PXXIV were not tested for these attributes, but were screened for ease of processability. The tables for the Prototypes below summarize the results.

Adhesive Screening. It is noted that most commercial modeling clays use some sort of binding agent to hold the structural matrix together. Most of the literature researched for modeling clay called for an adhesive such as PVOH to be the binder. Several other adhesives were also evaluated to assess their ability to improve the structure of the clay soap bar. The adhesives were screened by preparing simple systems of clay and adhesive and testing for their color, hardness, and surface texture. Color and texture were primarily evaluated to assess the aesthetics of the bar with the different types of surfactants.

Color Rating

| Rating | Description |
|---|---|
| 1 | White |
| 2 | Off-white |
| 3 | Grey |
| 4 | Dark Grey |

Hardness Rating

| Rating | Description |
|---|---|
| 1 | Very hard; Unbreakable by hand, need sharp object to break |
| 2 | Hard; Requires a lot effort to break |
| 3 | Moderate; Requires moderate effort to break |
| 4 | Soft; Requires slight or almost no effort to break |

Evaluation of Adhesive Screening Samples

| | 1 MagiGlue ™ | 2 AQ 38S | 3 AQ 55S | 4 Celvol ™ 205 | 5 GRS-9623-30 |
|---|---|---|---|---|---|
| Color | 2 | 1 | 1 | 1 | 3 |
| Hardness | 2 | 3 | 3 | 1 | 4 |

-continued

| | 1<br>MagiGlue ™ | 2<br>AQ 38S | 3<br>AQ 55S | 4<br>Celvol ™ 205 | 5<br>GRS-9623-30 |
|---|---|---|---|---|---|
| Surface Texture | Grainy material visible, due to inhomogeneous composition of MagiGlue ™ | Glossy surface, due to AQ polymer film formation | Glossy surface, due to AQ polymer film formation | Smooth, although not glossy like AQ based samples | Very soft and smooth |
| Notes on prep. | Sample was easy to form, requiring no adhesvie preparation | Adhesive solution was easily mixed with the clay to produce neat product | Same as AQ 38S but more difficult | Sample required more rigorous mixing to homogenize | Grease was easily incorporated into the clay |

It is noted that:

MagiGlue™ (activated by adding water and then allowing to dry) was very easy to incorporate into the clay bar formula and improved the structure of the bar. The use of MagiGlue™, however, left noticeable grainy specks in the composition due to its in-homogenous nature. In addition, hydrated MagiGlue™ darkened in color, which in turn darkened the composition of the final bar product.

The sulfopolyesters, AQ 38S and AQ55S, performed similarly upon initial testing. Although the molecular structures of these polymers are very similar, their Tg or glass transition temperatures, were very different. Since AQ 38S has a lower Tg, it required less heat and mixing to fully disperse in solution. Among the adhesives, the sulfopolyesters formed a glossy thin film on the surface of the bar, which was aesthetically appealing to observers. In relation to the PVOH polymer, the sulfopolyester solutions were much easier to prepare and incorporate into the clay. However, the AQ based clay bar structures were not as hard.

The Celvol™ 205 adhesive is part of a family of molecules called polyvinyl alcohol (PVOH) polymers. Celvol™ 205 performed the best of the adhesives in terms of hardness, indicating its ability to structure the clay bar. Moreover, it did not visually change the color or visual appearance of the bar. Using Celvol™ 205 did, however, require vigorous mixing under controlled heat to create the adhesive solution. The resulting solution was also very viscous, making incorporation into the clay a difficult task. The viscosity of the PVOH solutions exponentially increased with increasing concentration of the polymer.

Adhesive Concentration Study. Adhesive based concentrations studies were conducted to evaluate how adhesives impacted bar soap color, hardness, and dispersion rates.

Adhesive Impact on Color and Hardness of Adhesive Concentration Study Samples

The Effect of Adhesive on % Dispersion

| | % Dispersed | | | | |
|---|---|---|---|---|---|
| Sample | 30 min | 1 hr | 1.5 hrs | 2 hrs | 3 hrs |
| 6-MagiGlue ™ | <5 | <5 | ~5 | ~7-8 | ~10 |
| 7-MagiGlue ™ | <5 | <5 | <5 | <5 | ~5 |
| 8-AQ 38S | ~30 | ~90 | 100 | — | — |
| 9-AQ 38S | ~10 | ~20 | ~30 | ~55 | ~80 |
| 10-Celvol ™ 205 | <5 | ~5 | ~10 | ~20 | ~30 |
| 11-Celvol ™ 205 | <5 | <5 | <5 | ~5 | ~10 |

At the low concentrations (1-2.5% adhesive)

The MagiGlue™ sample held the composition together very well when left submerged in water; however the samples broke apart very easily. The low dispersion rate (only ~5-10% dispersed at 3 hours) gives us insight into the relationship between dispersibility and hardness. It seems that hardness is not the only major factor in determining the dispersibility of the bar. Grainy specks noted in previous screening experiments were also noticeable even at low concentrations.

AQ 38S containing bars had the lowest relative performance of the serial samples made, dispersing rapidly underwater and easily cracking. A glossy film on the surface of the samples was also noticeable at low concentrations.

For Celvol™ sample, the structural integrity of the bar is comparable to the MagiGlue™ sample in terms of dry hardness, however the bar structure quickly collapsed after 1 hour when submerged in water.

At high concentrations (5-12.5% adhesive):

MagiGlue™ showed noticeably enhanced structuring capability as evidenced by the increased hardness and lower dispersion rate of the bar.

AQ 38S did show noticeably enhanced performance with increased concentration, however it still did not perform as well as MagiGlue™ and PVOH in terms of bar structuring.

Celvol™ 205 performed very well in terms of hardness, color, and dispersibility properties. This indicates that

| | 6 | 7 | 8 | 9 | 10 | 11 |
|---|---|---|---|---|---|---|
| Adhesive | 2.5% MagiGlue ™ | 12.5% MagiGlue ™ | 1% AQ 38S | 5% AQ 38S | 1% Celvol ™ 205 | 5% Celvol ™ 205 |
| Color | 1 | 2 | 1 | 1 | 1 | 1 |
| Hardness | 3 | 1 | 3 | 2 | 2 | 1 |

PVOH can be a viable binder that does not affect the visual aesthetics of the clay bar like MagiGlue™. However, this raw material was exceptionally difficult to incorporate into the composition.

Overall:

MagiGlue™ was best at reducing the dispersion properties of the bar, whereas, AQ 38S was the least effective at holding the composition together when submerged in water. This may be attributed to the ionic sulfate groups on the AQ sulfopolyesters, which makes this material more water soluble. Currently, the superior performance of MagiGlue™ in this test cannot be explained due to the proprietary composition of the adhesive. It is theorized that the glue contains longer starch chains that may be hydrophobic.

AQ 38S exhibited good overall performance in terms of color and aesthetics and was relatively easy to incorporate into the clay compositions. Also, the unique aesthetics of the AQ polymer and natural aspect of MagiGlue™ could provide additional benefits to the clay bar such as increased improvements in the visual aesthetics.

Kaolin Clay Soap Bar Prototypes were evaluated for lather, color, hardness, surface texture, and density in comparison to Dove™ brand bar soap.

Evaluation of Kaolin Based Clay Soap Prototypes

| Observations | 12 | 13 | 14 |
|---|---|---|---|
| Lather* | | | |
| Quickness | parity | faster | faster |
| Quantity | less | greater | greater |
| Quality | parity† | parity† | parity† |
| Physical Features | | | |
| Color | 2 | 2 | 3 |
| Hardness | 2 | 2 | 2 |
| Surface Texture | glossy, smooth | glossy, smooth | slightly speckled |
| Density | 2.6 g/cc | 2.6 g/cc | 2.6 g/cc |

*Evaluated in comparison with Dove ™ Brand bar soap.
†Evaluators noted that there was a noticable difference between Dove ™ and prototypes, however agreed that both have soft and luxurious foam.

The table above illustrates the lather and physical characteristics of kaolin based bar soaps. Based on the lather results, the SLS/DDBS/CAPB/CMEA surfactant clay bar prototype was found to produce very luxurious and creamy lather. The lather was found to last noticeably longer than that produced by the Dove™ soap standard. It was also found that the concentration of SLS was directly proportional to the amount of flash foam generated.

Panelists noted a slightly sticky skin feel after washing and toweling dry with the above kaolin based prototypes. This observation was much less noticeable when higher surfactant concentrations were used presumably because the surfactants removed the adhesive on the skin. The type of binder had minimal influence on the level of stickiness.

The hardness of the prototype bars was acceptable and the bars were not easily broken. The surfactant containing bars were noticeably darker than the samples containing only clay and adhesive (Table 14). However, after a single wash, the bars assumed a white color resembling the color of the kaolin clay.

The AQ polymer was found to impart a characteristic glossy thin film to the bar, making the AQ based prototypes aesthetically more pleasing. This effect was not observed for the MagiGlue™ based prototype. The bars were also found to be quite dense (2.6 g/cc) compared to that of equivalent sized soap bars. This effect was attributed to the high density of packed kaolin clay (2.5 g/cc-2.7 g/cc).

The kaolin prototype bars displayed a high affinity for water. Consequently, when a wetted bar was removed from the soap dish, a significant amount of residue was left in the soap dish. The wetted bar was also found to leave a white residue on any surface it came into contact with, including the skin when handling. There are many potential causes to this problem, including the poor binding ability of the adhesives in a wet environment, the hydrophilic nature of clay, the usage of high amounts of surfactant, or a combination of the above.

The following bars I-XXXII are prepared by: 1. Add formula amounts (if present) of palm kernel oil, CMEA, glycerin, hydrogenated soybean oil, and stearyl alcohol to a batch vessel. 2. Heat this mixture to 71° C. (160° F.) with agitation. 3. Add formula amounts (if present) of SLES, SCI, Polyox™ WSR-N 750, soap chips, and talc and mix for 15 minutes. 4. Add clay and $TiO_2$ (0.2-0.5 weight %) and mix for 15 minutes. 5. Add tap water and continue mixing for 30 minutes. 6. Inspect batch for uniformity (should be in the form of pellets), 7. Remove batch from the mixer and weigh to determine yield. 8. Mill batch 2×-3× to fully incorporate the ingredients. Milling is more effective in fully incorporating the formula ingredients and producing a homogenous mixture for downstream refining and extrusion.

Some of the bars were compared to a commercially available Irish Spring™ with Aloe soap bars from Colgate-Palmolive, which represents a typical, commercially available soap bar.

| | I | II | III | IV | V | VI | VII | VIII |
|---|---|---|---|---|---|---|---|---|
| Kaolin | 66.56 | 69.8 | 35 | 68 | 68 | 59.79 | 59.75 | 57.3 |
| Talc | 11.09 | 10.66 | 15 | 15 | 14.8 | 22.05 | 21.9 | 22 |
| Glycerin | 5.76 | 5.04 | 4.9 | 5 | 5.3 | 3.13 | 3.18 | 3 |
| Sodium laureth sulfate, 70% | 16.59 | 14.5 | 10.1 | 12 | 11.9 | 15.03 | 15.05 | 17.5 |
| ModelingClay-Acrylic (Magic Mud ™) | | | 35 | 0 | | | | |
| Polyox ™ WSR-N 750 | | | | | | | 0.12 | 0.2 |
| Total | 100 | 100 | 100 | 100 | 100 | 100 | 100 | 100 |
| Lather | | | | | | | | |
| Low | | | X | X | X | | | |
| Moderate | | X | | | | X | X | |
| Voluminous | X | | | | | | | X |

-continued

| | Texture | | | | | | | | |
|---|---|---|---|---|---|---|---|---|---|
| Course | X | X | X | X | X | | | | |
| SlightlyGrainy | | | | | | X | X | | |
| Smooth | | | | | | | | X | |

| | Use-Up | | | | | | | | |
|---|---|---|---|---|---|---|---|---|---|
| <IrishSpringAloe | | | | | | | | X | |
| Parity | | | | | | | | | |
| >IrishSpringAloe | X | | | X | X | X | | | |

| | IX | X | XI | XII | XIII | XIV | XV | XVI | XVII |
|---|---|---|---|---|---|---|---|---|---|
| Kaolin | 57.1 | 56.23 | 37.2 | 42.2 | 47.2 | 52.2 | 51.2 | 51.2 | 56.2 |
| Talc | 22 | 21.68 | 22 | 22 | 22 | 22 | 22 | 22 | 22 |
| Glycerin | 3 | 4.59 | 3 | 3 | 3 | 3 | 3 | 3 | 3 |
| Sodium laureth sulfate, 70% | 17.5 | 17.19 | 17.5 | 17.5 | 17.5 | 17.5 | 17.5 | 17.5 | 17.5 |
| ModelingClay-Acrylic (Magic Mud ™) | | | | | | | | | |
| Polyox ™ WSR-N 750 | 0.4 | 0.31 | 0.3 | 0.3 | 0.3 | 0.3 | 0.3 | 0.3 | 0.3 |
| 80/20SoapChip | | | 20 | 15 | 10 | 5 | 5 | 5 | |
| Magnesium Sulfate | | | | | | | | 1 | 1 |
| Sodium Sulfate | | | | | | | | 1 | |
| Total | 100 | 100 | 100 | 100 | 100 | 100 | 100 | 100 | 100 |

| | Lather | | | | | | | | |
|---|---|---|---|---|---|---|---|---|---|
| Low | | | | | | | | | |
| Moderate | | | | | | | | | |
| Voluminous | X | X | X | | | | | | |

| | Texture | | | | | | | | |
|---|---|---|---|---|---|---|---|---|---|
| Course | | | | | | | | | |
| SlightlyGrainy | | | | | | | | | |
| Smooth | X | X | X | | | | | | |

| | Use-Up | | | | | | | | |
|---|---|---|---|---|---|---|---|---|---|
| <IrishSpringAloe | | | | | | | | | |
| Parity | X | X | X | | | | | | |
| >IrishSpringAloe | | | | | | | | | |

| | XVIII | XIX | XX | XXI | XXII | XXIII | XXIV | XXV |
|---|---|---|---|---|---|---|---|---|
| Kaolin | 56.2 | 53.34 | 53.09 | 58.53 | 56.4 | 50 | 54 | 52 |
| Talc | 22 | 20.62 | 20.6 | 20.6 | 20.6 | 24 | 20 | 24 |
| Glycerin | 3 | 3.75 | 3 | 3 | 3 | 4 | 4 | 4 |
| Sodium laureth sulfate, 70% | 17.5 | 16.48 | 17.5 | 17.5 | 17.5 | 20 | 20 | 17.5 |
| ModelingClay-Acrylic (Magic Mud ™) | | | | | | | | |
| Polyox ™ WSR-N 750 | 0.3 | 0.37 | 0.37 | 0.37 | 0.37 | 0.4 | 0.4 | 0.4 |
| Sodium Sulfate | 1 | | | | | | | |
| Tap Water | | 5.44 | 5.44 | | 2.13 | 1.6 | 1.6 | 2.1 |
| Total | 100 | 100 | 100 | 100 | 100 | 100 | 100 | 100 |

| | XXVI | XXVII | XXVIII | XXIX | XXX | XXX-A | XXX-B | XXXI |
|---|---|---|---|---|---|---|---|---|
| Kaolin | 50.4 | 50.9 | 50 | 52.7 | 49.8 | 52.4 | 58 | 57 |
| Talc | 13 | 10.1 | 12.5 | 10 | 10 | 15.4 | 9 | 9 |
| Glycerin | 2.4 | 2 | 1 | 1 | 1 | 1.95 | 1 | 1 |
| Sodium laureth sulfate, 70% | 8.2 | 7 | 12 | 7 | 8 | 10.11 | 8 | 10 |
| Polyox ™ WSR-N 750 | 0.3 | 0.4 | 0.3 | 0.3 | 0.2 | 0 | 0 | 0 |
| Tap Water | 14.9 | 10.6 | 12.2 | 15 | 15 | 5.44 | 9 | 9 |
| Cocomonoethanol amide | 0 | 2 | 2 | 3 | 5 | 1.83 | 5 | 5 |
| Sodium cocoyl isethionate | 5.7 | 10 | 3 | 4 | 2 | 4.59 | 2 | 2 |
| Hydogenated Soybean Oil | 5.1 | 4.5 | 4.5 | 4.5 | 3 | 2.76 | 2.5 | 3 |
| Palm kernel oil | 0 | 2.5 | 2.5 | 2.5 | 3 | 2.76 | 2.5 | 2 |
| Stearyl alcohol | 0 | 0 | 0 | 0 | 3 | 2.76 | 3 | 2 |
| Total | 100 | 100 | 100 | 100 | 100 | 100 | 100 | 100 |

| | XXXII | XXXIII | XXXIV | XXXV | XXXVI | XXXVII |
|---|---|---|---|---|---|---|
| Kaolin | 55 | 57 | 56 | 55 | 57 | 55.7 |
| Talc | 10 | 9 | 9 | 7 | 7 | 7 |
| Glycerin | 0 | 1 | 0 | 0 | 0 | 1 |
| Sodium laureth sulfate, 70% | 12 | 10 | 10 | 12 | 12 | 12 |
| Polyox ™ WSR-N 750 | 0 | 0 | 0 | 0 | 0 | 0.3 |
| Tap Water | 11 | 11 | 13 | 14.5 | 14.5 | 14.5 |

-continued

|  |  |  |  |  |  |  |
|---|---|---|---|---|---|---|
| Cocomonoethanol amide | 5 | 5 | 7 | 3.5 | 3.5 | 2 |
| Sodium cocoyl isethionate | 0 | 0 | 0 | 1.5 | 1.5 | 3 |
| Hydogenated Soybean Oil | 3 | 3 | 1 | 6 | 4 | 4 |
| Palm kernel oil | 2 | 2 | 0 | 0 | 0 | 0 |
| Stearyl Alcohol | 0 | 0 | 0 | 0 | 0 | 0 |
| Behenyl Alcohol | 2 | 0 | 1 | 0.5 | 0.5 | 0.5 |
| Total | 100 | 100 | 100 | 100 | 100 | 100 |

|  | XXXVII | XXXIX | XXXX | XXXXI | XXXXI-A | XXXXI-B |
|---|---|---|---|---|---|---|
| Kaolin | 55.7 | 56.5 | 40 | 55 | 44 | 45 |
| Talc | 7 | 8.45 | 28.2 | 10 | 22 | 22 |
| Glycerin | 1 | 0 | 0 | 0 | 0 | 0 |
| Sodium laureth sulfate, 70% | 12 | 12 | 10 | 10 | 12 | 10 |
| Polyox ™ WSR-N 750 | 0.3 | 0.3 | 0.3 | 0 | 0 | 0 |
| Tap Water | 14.5 | 12 | 7 | 5 | 5 | 5 |
| Cocomonoethanol amide | 5 | 5 | 7 | 4 | 4 | 4 |
| Sodium cocoyl isethionate | 0 | 0 | 0 | 0 | 2 | 2 |
| Hydrogenated Soybean Oil | 4 | 5.25 | 5 | 5 | 5 | 5 |
| Palmac 98-12 | 0 | 0 | 2 | 7 | 2 | 2 |
| White Ozokerite Wax | 0 | 0 | 0 | 4 | 4 | 5 |
| Behenyl Alcohol | 0.5 | 0.5 | 0.5 | 0 | 0 | 0 |
| Total | 100 | 100 | 100 | 100 | 100 | 100 |

|  | 3447 | 3447-A | 3447-B | 3447-C | 3447-D |
|---|---|---|---|---|---|
| Kaolin | 25 | 33 | 33 | 32.5 | 54 |
| Talc | 25 | 33 | 33 | 32.5 | 10 |
| Glycerin | 0 | 0 | 0 | 0 | 0 |
| Sodium laureth sulfate, 70% | 0 | 2 | 2 | 3.75 | 3.75 |
| Tap Water | 0 | 0 | 0 | 0 | 4 |
| Cocomonoethanol amide | 2 | 2 | 2 | 4 | 4 |
| Sodium cocoyl isethionate | 33 | 15 | 15 | 13 | 10 |
| Hydrogenated Soybean Oil | 0 | 0 | 0 | 4.75 | 4.75 |
| Palmac ™ 98-12 | 5 | 5 | 5 | 4.75 | 4.75 |
| White Ozokerite Wax | 5 | 5 | 5 | 4.75 | 4.75 |
| Stearyl Alcohol | 5 | 0 | 5 | 0 | 0 |
| Cetyl Alcohol | 0 | 5 | 0 | 0 | 0 |
| Total | 100 | 100 | 100 | 100 | 100 |

In addition to the examples above, the following examples are also prepared. For Formula XXVIII, an additional formula is prepared by mixing 75% by weight of Formula XXVIII with 25% by weight of a 85/15 soap. For Formula XXXIX, an additional formula is prepared by mixing 85% by weight of Formula XXXIX with 15% by weight of a 80/20 soap.

The slough and use up ratios of select formulas from above are compared against an 85/15 soap. The slough and use-up are evaluated as hydrophobic materials, such as hydrogenated soybean oil or behenyl alcohol, are added to see if slough and use-up are reduced. With the addition of hydrophobic materials, it is expected that the lathering would decrease. To compensate, soap systems and ratios are varied. In addition, a commercially available Dove moisture bar from the United States and a translucent soap bar are compared. The results are in the table below.

| Formula | Slough Ratio | Use Up Ratio |
|---|---|---|
| XVIII | 13.4 | 1.57 |
| XXVIII | 11.56 | 1.81 |
| 75% XXVIII 25% 85/15 soap | 7.89 | 2.11 |
| XXXVII | 9.8 | 1.57 |
| XXXVIII | 7.77 | 1.26 |
| XXXIX | 5.3 | 1.34 |
| 85% XXXIX 15% 80/20 soap | 6.59 | 1.38 |

-continued

| Formula | Slough Ratio | Use Up Ratio |
|---|---|---|
| XXXXI | 3.09 | 1.03 |
| XXXXIA | 6.84 | 2.22 |
| XXXXIB | 2.96 |  |
| 3447 | 0.97 | 0.88 |
| 3447-A | 1.66 | 0.89 |
| 3447-B | 1.27 | 0.95 |
| 3447-C | 1.68 | 1.16 |
| 3447-D | 2.83 | 1.03 |
| Translucent soap | 2.35 | 1.25 |
| Dove ™ moisture bar | 1.63 | 1.13 |

In the 3447 to 3447-D formulas, when water and the sodium laureth sulfate are replaced with SCI (sodium cocoyl isethionate, a solid surfactant), parity slough and use-up are achieved, but the cost increases. Replacing the SCI with sodium laureth sulfate can achieve comparable slough.

In Formula XXXXIB, high levels of sodium laureth sulfate are used for lather with high levels of hydrogenated soybean oil being used for structuring. Addition of cocomonoethanol amide and SCI increase the lather.

The following materials were used in the following examples.

1.2 Fillers

| Manufacturer | Product Name | Type |
| --- | --- | --- |
| KaMin ™ Performance Minerals | Polygloss ™ 90 | Kaolin |
| KaMin ™ Performance Minerals | KaMin ™ HG90 | Kaolin |
| Barretts Minerals, Inc. | Talc | Talc |
| Argiletz S.A. | Kaolinite White Clay | Kaolin |

1.2 Surfactants

| Manufacturer | Product Name | Type |
| --- | --- | --- |
| Clariant | Cocoamidopropyl Betaine (CAPB) | Cocamidopropyl Betaine |
| Clariant | Hostapon ™ SCI-65 | Sodium Cocoyl Isethionate (and) Stearic Acid |
| Cognis | Comperlan ™ 100 (CMEA) | Cocomonoethanolamide |
| Stepan Chemicals Co. | Steol ™ OS-270 (SLES, 70%) | Sodium laureth sulfate (2EO) (70%) |
| Finetex Inc. | Tauronol ™ SCMI-85 | Sodium cocoyl methyl isethionate |
| BASF | Pluronic ™ F108 | EO-PO block copolymer |
| Stepan Chemical Co. | Stepanol ™ WA-10 NF/USP (SLS) | Sodium lauryl sulfate (97%) |

1.2 Waxes and Oils

| Manufacturer | Product Name |
| --- | --- |
| Acidchem Intl. | Palmac ™ 98-12 (lauric acid) |
| Croda | Syncrowax ™ HRC (tribehenin) |
| Croda | Syncrowax ™ HGL-C (C18-36 Acid Triglyceride) |
| Cargill | RBD Palm Kernel Oil |
| Cargill | Hydrogenated Soybean Oil |
| Honeywell | Asensa ™ PR210 (Polyethylene (and) Stearic Acid) |
| Honeywell | Asensa ™ CL300 (Ethylene/VA Copolymer) |
| Strahl & Pitsch, Inc. | White Ozokerite Wax |
| Strahl & Pitsch, Inc. | Microcrystalline Wax |
| Strahl & Pitsch, Inc. | Paraffin Wax |
| Strahl & Pitsch, Inc. | Beeswax |
| Strahl & Pitsch, Inc. | Ceresine Wax |

1.2 Additives and Miscellaneous

| Maufacturer | Product Name | Material |
| --- | --- | --- |
| Croda | Crodamol ™ MM | Myristyl Myristate |
| BASF Co. | | Titanium Dioxide |
| Acidchem Intl. | | Glycerin |
| Dow Chemical Co. | Polyox ™ WSR-N 750 | PEG-7M |
| Athena Environmental Sciences | MagiGlue ™ | adhesive |
| Eastman | AQ 38S | Polyester-5 (sulfopolyester polymer) |
| Celanese | Celvol ™ 305 | Polyvinyl alcohol |

The following procedures were used to make the examples.

1. Lab Scale
   1.1 Weigh out formula amounts of the meltable ingredients in a mortar and heat to ~60-80° C. to melt. Maintain this elevated temperature throughout preparation process. Mix well with pestle until molten liquid is homogenous. Meltable ingredients include:
      a. Sodium Cocoyl Isethionate
      b. Coconut Fatty Acid Monoethanolamide (CMEA)
      c. Any fatty acids/oils—Palm Kernel Oil (PKO), Hydrogenated Soybean Oil (H-Soy), etc.
      d. Wax—Ceresin, White Ozokerite, Polyethylene (Asensa™ PR210), etc.
   1.2 Weigh out formula amounts of Talc and other non-soluble solid additives. Add the weighed materials to the molten liquid prepared previously and mix well with pestle until homogenous. Non-soluble solid additives may include:
      a. Polyox™ WSR N-750
      b. Titanium Dioxide (TiO$_2$)
   1.3 Weigh out formula amount of clay and add to the doughy liquid mixture formed in previous step. Mix the clay into the mixture vigorously with pestle for at least 10 minutes until homogenous composition is attained.
   1.4 Add in measured formula amounts of liquid surfactant and other room temperature liquids to the dough formed in previous stage. Mix rigorously again until homogenous. Liquids added in this stage include;
      a. 70% Sodium Laureth Sulfate
      b. 30% Cocoamidopropyl Betaine (CAPB)
      c. Glycerin
      d. DI Water
   1.5 Once dough-like mixture is mixed thoroughly, press into miniature bar shape using hands.
2. Pilot Plant Scale
   2.1 Weigh out formula amounts of the meltable ingredients a large 2 liter mortar and heat to ~60-80° C. using hot plate to melt. Maintain this elevated temperature throughout preparation process. Mix well. Meltable ingredients include:
      a. Sodium Cocoyl Isethionate (SCI, SCI-65, etc.)
      b. Coconut Fatty Acid Monoethanolamide (CMEA)
      c. Any fatty acids/oils—Palm Kernel Oil (PKO), Hydrogenated Soybean Oil (H-Soy), etc.
      d. Wax—Ceresin, White Ozokerite, Polyethylene (Asensa™ PR210), etc.
   2.2 Weigh out formula amounts of filler material (i.e. clay and talc) and other non-soluble solid additives. Add the weighed materials to the molten liquid prepared previously and mix well with pestle. Non-soluble solid additives may include:
      a. Polyox™ WSR N-750
      b. Titanium Dioxide (TiO$_2$)
   2.3 Add in measured formula amounts of liquid surfactant and other room temperature liquids to the dough formed in previous stage. Mix rigorously again until homogenous. Liquids added in this stage include:
      a. 70% Sodium Laureth Sulfate
      b. 30% Cocoamidopropyl Betaine (CAPB)
      c. Glycerin
      d. DI Water 2.4 Once dough-like mixture is mixed thoroughly, send the material through the extruder to create billets.
2.5 Press the billets using the soap press to create bars.

The following formulations were prepared using the procedures above.

Formulations for Preliminary Wax-Clay Bar Trials

| Ingredients | A wt % | B wt % | C wt % |
|---|---|---|---|
| Polygloss ™ 90 | 50 | 60 | 60 |
| Paraffin Wax | 50 | 22 | 12 |
| Myristyl Myristate | 0 | 5 | 4 |
| 70% SLES | 0 | 11 | 20 |
| Pluronic ™ F108 | 0 | 1.5 | 3 |
| CMEA | 0 | 0.5 | 1 |
| Σ | 100 | 100 | 100 |

Formulations for Lab Scale Batch Preparation Assessments

| Ingredients | D wt % | E wt % | F wt % |
|---|---|---|---|
| Polygloss ™ 90 | 60 | 60 | 60 |
| Paraffin Wax | 22 | 22 | 22 |
| SCMI-85 | 0 | 0 | 16 |
| 70% SLES | 16 | 16 | 0 |
| Pluronic ™ F108 | 1.5 | 1.5 | 1.5 |
| CMEA | 0.5 | 0.5 | 0.5 |
| Σ | 100 | 100 | 100 |

Formulations for Filler Assessment

| Ingredients | wt % G | wt % H |
|---|---|---|
| Polygloss ™ 90 | 45 | 0 |
| Talc | 20 | 65 |
| Polyox ™ WSR-N 750 | 1 | 1 |
| Ceresine Wax | 15 | 15 |
| SCMI-85 | 16 | 16 |
| CMEA | 3 | 3 |
| Σ | 100 | 100 |

| Ingredients | I | J |
|---|---|---|
| Talc | 65 | 62 |
| Ceresine Wax | 15 | 10.50 |
| CFA | 0 | 4.50 |
| 70% SLES | 16 | 16 |
| CMEA | 1 | 3 |
| Polyox ™ WSR-N 750 | 1 | 0 |
| Glycerin | 2 | 2 |
| DI Water | 0 | 2 |
| Σ | 100 | 100 |

Formulations for Wax Type Studies

| Ingredient | K wt. % | L wt. % | M wt. % | N wt. % | O wt. % | P wt. % | Q wt. % |
|---|---|---|---|---|---|---|---|
| KaMin ™ HG90 | 50 | 50 | 50 | 50 | 50 | 50 | 50 |
| Talc | 15 | 15 | 15 | 15 | 15 | 15 | 15 |
| Glycerin | 2 | 2 | 2 | 2 | 2 | 2 | 2 |
| White Ozokerite Wax | 5 | 0 | 0 | 0 | 0 | 0 | 0 |
| Microcrystalline Wax | 0 | 5 | 0 | 0 | 0 | 0 | 0 |
| Paraffin Wax | 0 | 0 | 5 | 0 | 0 | 0 | 0 |
| Asensa ™ PR210 | 0 | 0 | 0 | 5 | 0 | 0 | 0 |
| Asensa ™ CL300 | 0 | 0 | 0 | 0 | 5 | 0 | 0 |
| H-Soybean Oil | 0 | 0 | 0 | 0 | 0 | 5 | 0 |
| Syncrowax ™ HGL-C | 0 | 0 | 0 | 0 | 0 | 0 | 5 |
| Palmac ™ 98-12 | 1 | 1 | 1 | 1 | 1 | 1 | 1 |
| 70% SLES | 9 | 9 | 9 | 9 | 9 | 9 | 9 |
| SCI-65 | 4 | 4 | 4 | 4 | 4 | 4 | 4 |
| CMEA | 2 | 2 | 2 | 2 | 2 | 2 | 2 |
| DI Water | 12 | 12 | 12 | 12 | 12 | 12 | 12 |
| Total | 100 | 100 | 100 | 100 | 100 | 100 | 100 |

Formulations for Surfactant Assessment

| Ingredient | R wt % | S wt % | T wt % | U wt % | V wt % | W wt % | X wt % | Y wt % | Z wt % | AA wt % |
|---|---|---|---|---|---|---|---|---|---|---|
| KaMin ™ HG90 | 50 | 50 | 50 | 50 | 50 | 50 | 50 | 50 | 50 | 50 |
| Talc | 17 | 15 | 13 | 15 | 13 | 17 | 15 | 13 | 15 | 13 |
| Glycerin | 2 | 2 | 2 | 2 | 2 | 2 | 2 | 2 | 2 | 2 |
| Ceresine Wax | 3 | 3 | 3 | 5 | 5 | 3 | 3 | 3 | 5 | 5 |
| Palmac ™ 98-12 | 1 | 3 | 5 | 1 | 3 | 1 | 3 | 5 | 1 | 3 |
| 70% SLES-2EO | 9 | 9 | 9 | 9 | 9 | 12 | 12 | 12 | 12 | 12 |
| SCI-65 | 4 | 4 | 4 | 4 | 4 | 5 | 5 | 5 | 5 | 5 |
| CMEA | 2 | 2 | 2 | 2 | 2 | 3 | 3 | 3 | 3 | 3 |
| DI Water | 12 | 12 | 12 | 12 | 12 | 7 | 7 | 7 | 7 | 7 |
| Total | 100 | 100 | 100 | 100 | 100 | 100 | 100 | 100 | 100 | 100 |

Hydrogenated Soybean Oil Based Clay Bar Formulations

| Ingredients | AB wt % | AC wt % |
|---|---|---|
| Kaolin White Clay | 50.47 | 50 |
| Talc | 13.03 | 12.5 |
| Glycerine | 2.44 | 1 |
| SLES, 70% | 8.14 | 12 |
| Polyox ™ WSR-N 750 | 0.33 | 0.3 |
| Tap Water | 14.81 | 12.2 |
| Sodium Cocyl Isethionate | 5.7 | 3 |
| CMEA Flake | 0 | 2 |
| Hydrogenated Soybean Oil | 5.08 | 2.5 |
| Palm kernel oil | — | 4.5 |
| Total | 100 | 100 |

Formulations for Pilot Plant Studies

| Ingredients | AD wt % | AE wt % | AF wt % | AG wt % | AH wt % |
|---|---|---|---|---|---|
| KaMin ™ HG90 | — | — | 54.5 | 25 | 45 |
| Talc | 62 | 65 | 13.6 | 40 | 20 |
| Ceresine Wax | 10 | 3 | 2.7 | 3 | 5 |
| Palmac ™ 98-12 | 0 | 2 | 1.8 | 2 | 2 |
| 70% SLES | 13 | 12 | 10.9 | 12 | 12 |
| CMEA | 0 | 3 | 2.7 | 3 | 2 |
| CAPB | 8 | 5 | 4.5 | 5 | 4 |
| SCI-65 | 5 | 8 | 7.3 | 8 | 8 |
| Glycerin | 2 | 2 | 2 | 2 | 2 |
| Σ | 100 | 100 | 100 | 100 | 100 |

Formulations for Total Wax Assessment

| Ingredients | BA wt % | BB wt % | BC wt % | BD wt % | BE wt % | BF wt % |
|---|---|---|---|---|---|---|
| Polygloss 90 | 40 | 0 | 0 | 0 | 0 | 0 |
| Talc | 20 | 65 | 60 | 59 | 59 | 60 |
| Polyox ™ WSR-N 750 | 1 | 1 | 0 | 0 | 0 | 0 |
| Ceresine Wax | 20 | 15 | 12 | 10 | 3 | 2 |
| Syncrowax ™ HRC Wax | 0 | 0 | 0 | 1 | 0 | 0 |
| Ceraphyl ™ 65 | 0 | 2 | 0 | 0 | 0 | 0 |
| SLS Powder | 0 | 0 | 0 | 3 | 0 | 0 |
| SCI-65 | 0 | 0 | 10 | 4.5 | 14 | 14 |
| CAPB | 0 | 0 | 6 | 7 | 5 | 5 |
| 70% SLES | 16 | 16 | 10 | 10 | 15 | 15 |
| Glycerin | 0 | 0 | 2 | 4 | 2 | 2 |
| CMEA | 3 | 1 | 0 | 1.5 | 2 | 2 |
| Σ | 100 | 100 | 100 | 100 | 100 | 100 |

Formulations for Wax Content Studies

| Ingredient | CA wt % | CB wt % | CC wt % | CD wt % | CE wt % | CF wt % |
|---|---|---|---|---|---|---|
| KaMin ™ HG90 | 49 | 47.5 | 46 | 49 | 47.5 | 46 |
| Talc | 12.25 | 11.875 | 11.5 | 12.25 | 11.875 | 11.5 |
| Glycerin | 0.98 | 0.95 | 0.92 | 0.90 | 0.95 | 0.92 |
| SLES, 70% | 11.76 | 11.4 | 11.04 | 11.76 | 11.4 | 11.04 |
| Polyox ™ WSR-N750 | 0.294 | 0.285 | 0.276 | 0.294 | 0.285 | 0.276 |
| Hostapon ™ SCI-65 | 2.94 | 2.85 | 2.76 | 2.94 | 2.85 | 2.76 |
| Comperlan ™ 100 CMEA | 1.96 | 1.9 | 1.84 | 1.96 | 1.9 | 1.84 |
| RBD PKO | 2.45 | 2.375 | 2.3 | 2.45 | 2.375 | 2.3 |
| Hydrogenated Soybean Oil | 4.41 | 4.275 | 4.14 | 4.41 | 4.275 | 4.14 |
| White Ozokerite Wax | 2 | 5 | 8 | 0 | 0 | 0 |
| Asensa ™ PR210 | 0 | 0 | 0 | 2 | 5 | 8 |
| Tap Water | q.s. | q.s. | q.s. | q.s. | q.s. | q.s. |
| Total | 100 | 100 | 100 | 100 | 100 | 100 |

Formulations for Palm Kernel Oil Assessment

| Ingredient | DA wt % | DB wt % | DC wt % | DD wt % | DD wt % | DE wt % |
|---|---|---|---|---|---|---|
| KaMin ™ HG90 | 50 | 50 | 50 | 50 | 50 | 50 |
| Talc | 15 | 15 | 15 | 15 | 15 | 15 |
| Polyox ™ WSR-N750 | 0.3 | 0.3 | 0.3 | 0.3 | 0.3 | 0.3 |
| Glycerin | 1 | 1 | 1 | 1 | 1 | 1 |
| SLES, 70% | 12 | 14 | 12 | 14 | 12 | 12 |
| Hostapon ™ SCI-65 | 3 | 4 | 3 | 4 | 3 | 3 |
| Comperlan ™ 100 CMEA | 2 | 3 | 2 | 3 | 2 | 2 |
| RBD PKO | 2.5 | 2.5 | 0 | 2.5 | 2.5 | 0 |
| Hydrogenated Soybean Oil | 4.5 | 4.5 | 5 | 4.5 | 4.5 | 5 |
| White Ozokerite Wax | 5 | 5 | 5 | 5 | 5 | 5 |
| DI Water | q.s. | q.s. | q.s. | q.s. | q.s. | q.s. |
| Total | 100 | 100 | 100 | 100 | 100 | 100 |

Formulations for Palm Kernel Oil Assessment

|  | Sample | | | | |
|---|---|---|---|---|---|
| Ingredient | EA wt % | EB wt % | EC wt % | ED wt % | EE wt % |
| KaMin ™ HG90 | 50 | 50 | 50 | 50 | 50 |
| Talc | 15 | 15 | 15 | 15 | 15 |
| Polyox ™ WSR-N750 | 0.3 | 0.3 | 0.3 | 0.3 | 0.3 |
| Glycerin | 1 | 1 | 1 | 1 | 1 |
| SLES, 70% | 12 | 12 | 12 | 12 | 12 |
| Hostapon ™ SCI-65 | 3 | 3 | 3 | 3 | 3 |
| Comperlan ™ 100 CMEA | 2 | 2 | 2 | 2 | 2 |
| RBD PKO | 1 | 0.5 | 2 | 0 | 0 |
| Hydrogenated Soybean Oil | 4.5 | 4.5 | 4 | 4 | 2 |
| White Ozokerite Wax | 5 | 5 | 5 | 5 | 5 |
| DI Water | q.s. | q.s. | q.s. | q.s. | q.s. |
| Total | 100 | 100 | 100 | 100 | 100 |

Other Formulas

| Ingredients | ZA wt % | ZB wt % | BA wt % | ZC wt % | G wt % | H wt % |
|---|---|---|---|---|---|---|
| Polygloss 90 | 40 | 40 | 40 | 40 | 45 | 0 |
| Talc | 20 | 20 | 20 | 20 | 20 | 65 |
| Polyox ™ WSR-N750 | 1 | 1 | 1 | 1 | 1 | 1 |
| Ceresine Wax | 0 | 0 | 20 | 20 | 15 | 15 |
| Paraffin Wax | 20 | 20 | 0 | 0 | 0 | 0 |
| SCMI-85 | 0 | 0 | 0 | 16 | 16 | 16 |
| 70% SLES | 16 | 16 | 16 | 0 | 0 | 0 |
| Pluronic ™ F108 | 2 | 2 | 0 | 0 | 0 | 0 |
| CMEA | 1 | 1 | 3 | 3 | 3 | 3 |
| Σ | 100 | 100 | 100 | 100 | 100 | 100 |

| Ingredients | BB wt % | I wt % | ZD wt % | J wt % |
|---|---|---|---|---|
| Talc | 65 | 65 | 61 | 62 |
| Ceresine Wax | 15 | 15 | 8 | 11 |
| CFA | 0 | 0 | 8 | 5 |
| Ceraphyl ™ 65 | 2 | 0 | 0 | 0 |
| 70% SLES | 16 | 16 | 16 | 16 |
| CMEA | 1 | 1 | 3 | 3 |
| Polyox ™ WSR-N750 | 1 | 1 | 0 | 0 |
| Glycerin | 0 | 2 | 3 | 2 |
| DI Water | 0 | 0 | 3 | 2 |
| Σ | 100 | 100 | 100 | 100 |

| Ingredients | ZE wt % | ZF wt % | ZG wt % | BC wt % | ZH wt % | ZI wt % |
|---|---|---|---|---|---|---|
| Talc | 60 | 60 | 60 | 60 | 60 | 60 |
| Ceresine Wax | 10 | 10 | 10 | 12 | 12 | 10 |
| Palmac ™ 98-12 | 0 | 0 | 5 | 0 | 0 | 5 |
| 70% SLES | 0 | 5 | 5 | 10 | 13 | 12 |
| CAPB | 0 | 3 | 3 | 6 | 8 | 6 |
| SCI-65 | 28 | 20 | 15 | 10 | 5 | 5 |
| Glycerin | 2 | 2 | 2 | 2 | 2 | 2 |
| Total | 100 | 100 | 100 | 100 | 100 | 100 |

| Ingredients | ZJ wt % | BD wt % | ZK wt % |
|---|---|---|---|
| Talc | 59 | 59 | 59 |
| Ceresine Wax | 10 | 10 | 10 |
| Syncrowax ™ HRC | 1 | 1 | 1 |
| SLS Powder | 3 | 0 | 9 |
| 70% SLES | 10 | 13 | 0 |
| CAPB | 7 | 9 | 9 |
| CMEA | 2 | 0 | 0 |
| SCI-65 | 5 | 5 | 5 |
| Glycerin | 4 | 4 | 4 |
| DI Water | 0 | 0 | 4 |
| Σ | 100 | 100 | 100 |

| Ingredients | BE wt % | BF wt % | ZL wt % |
|---|---|---|---|
| Talc | 59 | 60 | 60 |
| Ceresine Wax | 3 | 2 | 2 |
| Palmac ™ 98-12 | 0 | 0 | 2 |
| 70% SLES | 15 | 15 | 17 |
| CMEA | 2 | 2 | 2 |
| CAPB | 5 | 5 | 5 |
| SCI-65 | 14 | 14 | 10 |
| Glycerin | 2 | 2 | 2 |
| Total | 100 | 100 | 100 |

Below are the results from the Preliminary Wax-Clay Bar Trials.

Lather

|  | A* | B | C |
|---|---|---|---|
| Generation | n/a | None | Fast |
| Amount | n/a | None | moderate high |
| Quality | n/a | None | large bubbles, non-creamy |
| Post-Wash Skin Feel | n/a | greasy, waxy | soft, but noticeable stickiness to skin after wash |

*No surfactants were added to this sample

Dispersibility

|  | A | B | C |
|---|---|---|---|
| initial | 0 | 0 | 0 |
| 30 min | 0 | 1 | 1 |
| 1 hr | 0 | 1 | 5 |
| 2 hrs | 0 | 3 | 20 |
| 3 hrs | 0 | 5 | >50 |
| 1 day | 0 | 10 | 100 |
| 3 days | 0 | >50 | — |

Data represents approximate loss in wt. %

It is noted that it is feasible to incorporate wax into the clay without the use of emulsifiers. The wax readily adsorbs onto the clay surface and simply requires mixing to cover the clay's surface with wax. There was a technical challenge in homogenizing the final mixture of the samples that contained surfactants due to the highly contrasting properties of the ingredients and the heat requirement throughout the preparation of the sample. This obstacle was overcome in the lab by vigorous mixing while maintaining the elevated temperature of the mortar throughout the process.

It is seen from sample B that high concentrations wax reduces the bar's ability to generate lather. It is also seen that a large concentration of surfactants in sample C allows the product to generate a sufficient amount of foam comparable to regular soap bars at the expense of the bar's stability in a wet environment.

Lab Scale Batch Preparation Assessments

For Formulation D, the procedure deviates from the protocol described above in that the surfactant and other liquids are added to the molten meltables prior to adding the filler material. The procedure is identical in the other steps.

Lather

|  | D | E | F |
|---|---|---|---|
| Generation* | Slow | Parity | Slow |
| Amount | Moderate | Moderate | Low-moderate |
| Quality | Loose, thin, medium sized bubbles | Loose, thin, large bubbles | Creamy, small bubbles |
| Post-Wash Skin Feel | Draggy skin feel when skin is still wet, clean skin feel when dry | Identical to D, slightly more clean feeling | Draggy skin feel when skin is still wet, smooth skin feel when dry |

*In comparison Palmolive bar soap

Dispersibility

|  | D | E | F |
|---|---|---|---|
| initial | 0 | 0 | 0 |
| 30 min | trace | 1 | trace |
| 1 hr | 1 | 2 | 1 |
| 2 hrs | 2 | 2 | 2 |
| 3 hrs | 3 | 3 | 5 |
| 1 day | 5 | 5 | 10 |
| 3 days | >50 | >50 | >50 |

Data represents approximate loss in wt. %

In this experiment, it is noted that the order of addition of ingredients makes an impact in the final properties of the bar. It was observed that adding surfactant after the clay has absorbed the wax to give better lather properties between the variations of preparation. It is theorized that this is due to fuller adsorption of the hydrophobic wax by the filler and lesser interaction between the surfactant and wax. Also, at this high concentration of wax, the change in order of addition of ingredients did not significantly impact the dispersibility of the prototypes.

Sodium cocoyl methyl isethionate (SCMI) was also screened along with sodium laureth sulfate (SLES) as the primary surfactant in the composition. SCMI was found to give creamier lather in comparison with SLES. However, the lather of SLES based prototypes was superior in terms of volume and quickness of lather. This result is expected based on the nature of the two types of surfactants.

Initial Formulation Work

In this work, the ranges of the ingredients were varied to find ratios of ingredients for further refinement. Different types of filler, wax, and surfactants were also assessed for their performance in the wax-clay bar system.

Lather

|  | G | H | I | J |
|---|---|---|---|---|
| Generation* | Parity | Parity | Slightly faster | Fast |
| Amount | Low-moderate | Low | Moderate | Low-moderate |
| Quality | Creamy, small bubbles | Creamy, small bubbles | Large bubbles initially, but quickly dissipates | Medium sized bubbles, quickly dissipates |
| Post-Wash Skin Feel | Moderate drag sensation, clean dry skin feel | Slight drag sensation, clean dry skin feel | Slight drag sensation, clean dry skin feel | Very slight drag sensation, very soft and clean skin feel |

*In comparison to Palmolive™ bar soap

Dispersibility

|  | G | H | I | J |
|---|---|---|---|---|
| initial | 0 | 0 | 0 | 0 |
| 30 min | trace | trace | trace | 2 |
| 1 hr | 1 | trace | 1 | 3 |
| 2 hrs | 2 | 1 | 2 | 5 |
| 3 hrs | 5 | 2 | 5 | 10 |
| 1 day | 20 | 10 | 10 | 30 |

In terms of lathering properties, it is noted that samples containing talc have a lower lather profile in relation to solely kaolin based bars. For example, compare the lather profiles of samples E (from previous experiment) and I, which have nearly identical surfactant composition, but differing in filler type. In comparison with the prototypes made in the previous experiment without talc and Polyox™ WSR-N 750, the bars made in this experiment decreased in the amount of drag and stickiness felt by the skin after washing. Looking at the properties of talc, it is noted that it is actually a slightly hydrophobic and very lipophillic type of clay. It is theorized that the decrease in wax dispensed on the skin to wax being adsorbed strongly onto the talc.

For the dispersibility characteristics, it is noted that for samples containing the same amount of wax, the use of talc improves the stability of the bar in water. From the results, it is noted that the effect of talc on the dispersion rate of the bar is not as significant as that of the wax and surfactant composition. Talc can aid in the balancing of the latter two ingredients in the formula for optimum dispersion characteristics.

It was also noted that the use of solely talc in the bar causes a softening of the bar in comparison to kaolin containing samples. Structure and lipophilic/hydrophilic differences between kaolin and talc attribute to this trend.

One of the effects with the wax-clay bar is the noticeable drag felt on the skin after washing with the bars. The drag sensation is attributed to the wax by comparing samples with and without wax, with otherwise identical composition. This sensation is only noted by panelists when the skin is still moist after washing. Thus, a range of wax content was investigated where there is sufficient wax to impart hydrophobicity to the clay bars without leaving the drag sensation.

Total Wax Content Studies. In this study, the total wax content was varied in the wax-clay bars from 2 to 20 wt %. The following chart gives the dispersibility data.

| | Wax % | | | | | |
|---|---|---|---|---|---|---|
| | 20% | 15% | 12% | 11% | 3% | 2% |
| | Sample | | | | | |
| Time | BA % disp. | BB % disp. | BC % disp. | BD % disp. | BE % disp. | BF % disp. |
| 0 | 0 | 0 | 0 | 0.5 | 0.5 | 0.5 |
| 30 | 0.5 | 0.5 | 0.5 | 1 | 3 | 3 |
| 60 | 1 | 0.5 | 1 | 2 | 7 | 7 |
| 90 | 1 | 1 | 2 | 3 | 10 | 10 |
| 120 | 2 | 2 | 3 | 5 | 30 | 30 |
| 180 | 5 | 5 | 5 | 10 | 50 | 70 |
| 1440 | 30 | 10 | 15 | 15 | 100 | 100 |

The data shows that with ≥10% wax content, the bars are highly water stable and there is little performance enhancement with increasing wax content. Also, from the data of the 2-5% samples, it is noted that the dispersion rates are relatively the same for the first 90 minutes before they begin to deviate. It is theorized that this relates to the time it takes for water to penetrate the inner parts of the bar and thus increase the surface area the water has to disperse the bar.

In this study, an assessment was made to determine quantitative data for the amount of wax deposited on the skin from the wax-clay bars. This was conducted by hand washing the bars with tared safety gloves (Neoprene type) and subsequently measuring the mass of the gloves afterwards to determine the weight change of the gloves. The data, however, was very inconsistent and cannot be directly related to deposition of wax on the skin. Thus, a panel of group members was used to qualitatively assess the drag sensation from each bar. The panelists were asked to hand wash with each bar. Palmolive™ bar soap was used in between each washing to remove the wax deposition from the trial samples. It is noted that there is a direct correlation between total wax content and drag sensation experienced by the panelists.

Wax type studies. In this study, 6 different waxes were screened and hydrogenated soybean oil (HSO) in the wax-clay bar system. The samples were prepared with identical composition other than wax type. The samples contained 5% of the wax, 50/15% of kaolin/talc, and 15% total surfactants. Samples prepared for this study are designated K-Q.

In terms of dispersibility, all of the samples performed almost equally, except for the HSO based sample, which fully disintegrated within 2 hours. This was expected, since HSO is more easily emulsified by the surfactants, thus negating its contribution to the hydrophobicity of the bar.

The same panelists from the total wax content study were also asked to assess any differences in terms of drag sensation from the bars. Response was highly varied, however, two samples containing White Ozokerite wax (a wax mixture from Strahl & Pitsch) and polyethylene wax (Asensa™ PR210 from Honeywell), respectively, were found to give the least drag sensation.

Surfactant Assessment. As noted before in the preliminary trials of the wax-clay bar, surfactant composition contributes considerably to the dispersion rate and consequently the water stability of the bar in addition to being the cleansing agent in the system. Various surfactant combinations were examined as well as total surfactant loads. Also, several additives were used to explore their uses in enhancing the lather profile of the wax-clay bar system.

From previous experiments, it is noted that samples containing less than 12% total surfactants produced little to no lather and samples containing greater than 20% total surfactants severely diminished the clay bar's stability in water. To keep the number of prototypes that needed to be made reasonable, total surfactant loads of 15% and 20% were selected with consistent ratios of the types of surfactants used. The surfactant system that has proven to work very well from the previous experiments is the SLES/SCI/CMEA combination at approximately 4:2:1 ratio, respectively. Also, it is noted that the lather profile is affected by the rest of the formulation, especially in the case of fatty acids, oils, and waxes. The variation of the samples was done by changing the wax/fatty acid ratio and content on both the 15% and 20% total surfactant samples. The following data table compares the lather performance of the samples in relation to Palmolive bar soap. The dispersibility results of the samples are also presented with a control sample of Palmolive bar soap.

| Sample | Total Composition Percentage | | | Lather | | |
|---|---|---|---|---|---|---|
| | Wax | Fatty Acids | Surfactants | generation | quantity | quality |
| R | 3 | 1 | 15 | + | = | = |
| S | 3 | 3 | 15 | + | = | + |
| T | 3 | 5 | 15 | − | − | = |
| U | 5 | 1 | 15 | + | − | = |
| V | 5 | 3 | 15 | = | − | − |
| W | 3 | 1 | 20 | ++ | + | + |
| X | 3 | 3 | 20 | + | = | + |
| Y | 3 | 5 | 20 | − | − | = |
| Z | 5 | 1 | 20 | + | + | + |
| AA | 5 | 3 | 20 | + | = | + |

Legend:
"+" better performance;
"=" parity performance;
"−" less performance

| Time | R % disp. | S % disp. | T % disp. | U % disp. | V % disp. | W % disp. | X % disp. | Y % disp. | Z % disp. | AA % disp. |
|---|---|---|---|---|---|---|---|---|---|---|
| 0 | 1 | 0 | 0 | 0 | 0 | 1 | 1 | 0 | 0 | 0 |
| 30 | 30 | 10 | 1 | 20 | 1 | 20 | 20 | 5 | 20 | 10 |
| 60 | 50 | 15 | 5 | 30 | 5 | 50 | 30 | 5 | 40 | 30 |
| 90 | 80 | 30 | 8 | 50 | 8 | 80 | 50 | 10 | 50 | 45 |
| 120 | 100 | 40 | 10 | 100 | 10 | 100 | 100 | 20 | 100 | 60 |
| 180 | 100 | 60 | 15 | 100 | 20 | 100 | 100 | 40 | 100 | 80 |

From the results, it was noted that performance of the bars can vary with the change in amount of free fatty acid (Palmac™ 98-12; $C_{12}$ fatty acid) added. With increasing fatty acid concentration, the bar became increasingly more water stable. There was, however, an associated decrease in lather quantity of the bars. From these results, it is hypothesized that the fatty acid works to increase the stability of the bar in water by interacting with the surfactants and limiting the extent of the surfactant-water interaction when submerged in water. The fact that there is a dramatic decrease in foam generation with increasing fatty acid concentration helps support this theory.

In comparing the effect of total surfactant percentage, it is noted that with balanced levels of fatty acid and wax, 15% total surfactants can perform on parity or with superior lather properties compared to the Palmolive™ bar soap (samples R & S). Samples with 20% total surfactants all had superior lather attributes except for the sample containing 5% fatty acid. It was also noted that the samples with 20% surfactants were less stable in water than samples containing only 15% surfactants.

It is noted that HSO performs very well in structurally binding the clay bar system without giving adverse effects on the lather profile of the bar. The bar, however, still has soap slough formation when left in a moist soap dish. From the results of prior work, wax was selected to improve the bar's stability in wet environments. The evaluation will use one set of formulations that avoids using wax to minimize processing difficulties and another set that employs wax to explore the benefits of wax inclusion.

Wax plus hydrogenated soybean oil based clay bars. From the wax assessment of previous work, it is noted that White Ozokerite wax and polyethylene wax (Asensa™ PR210) gave the lowest effect of "drag" and "sticky" skin feel after washing. Wax content was varied from 2-8 wt. % and was added to AC.

| | | | | Wax % | | | | |
|---|---|---|---|---|---|---|---|---|
| | | 0% | 20% | 15% | 12% | 10% | 3% | 2% |
| | | | | Sample | | | | |
| Time | Standard % disp. | AC % disp. | CA % disp. | CB % disp. | CC % disp. | CD % disp. | CE % disp. | CF % disp. |
| 0 | 0 | 1 | 1 | 1 | 1 | 1 | 1 | 1 |
| 30 | 0 | 10 | 10 | 3 | 3 | 10 | 3 | 1 |
| 60 | 2 | 30 | 10 | 5 | 5 | 15 | 5 | 5 |
| 90 | 5 | 50 | 15 | 12 | 10 | 20 | 15 | 10 |
| 120 | 8 | 80 | 40 | 15 | 15 | 30 | 20 | 20 |
| 180 | 10 | 100 | 50 | 30 | 20 | 50 | 30 | 30 |
| 240 | 13 | 100 | 60 | 50 | 30 | 80 | 50 | 50 |

As can be noted from above, the addition of wax into the bar improved the dispersibility rate of the HSO-based bars in comparison with Sample AC. Both types of waxes performed similarly. Qualitative lather assessment of the bars showed that the wax had a minor reduction of generation and quality of lather.

Pilot Plant Studies

The physical properties of the processed bars on the pilot plant scale are noticeably different than those made in the lab.

Hardness of the bars was one of the first attributes found to be noticeably different between samples made on the lab scale versus those made on the pilot plant scale. It is noted that that both water content and filler ratio makes the most significant impacts on the hardness of the bars.

During large scale mixing, the mixing times had to be extended to ensure homogeneity of the batch. Much of the water content contributed by the SLES is evaporated during this extended mixing period, thus extra water is required to replace the amount evaporated. The amount of extra water necessary varied greatly, depending both on the formulation and mixing parameters. In general, the lesser the total surfactant and wax/HSO used, the more water needed. Filler ratio of clay:talc was found to give the greatest hardness at approximately 10:3 ratio, resulting in 50/15 wt. % in the final formulation. Too much talc makes the bars soft and too little results in highly brittle finished bars.

Another observation of the pilot plant scale bars was their tendency to crack and form fissures around the perimeter of the bar, where the top and bottom of the soap press forms an edge on the bar. Any fissures would lead to easier access for water to penetrate and disperse the bar. It is noted that by adding small amounts of palm kernel oil in addition to HSO eliminated the fissures.

Moisturization Studies. In order to get an idea of how well the formulations stand in terms of skin moisturization, samples were tested against a standard of Palmolive™ bar soap. Pigskin moisturization studies were conducted on the following samples: R, S, AB, Control (Palmolive™ brand soap bar).

| Sample | Average Moisturization | P value |
|---|---|---|
| Control | 35.50 | — |
| AB | 39.40 | 0.0704 |
| R | 49.35 | 0.0088 |
| S | 38.35 | 0.0913 |

The results show that formulas remain better than regular toilet soaps.

Hydrophobic Ingredient Assessments. Hydrophobic ingredients currently employed in the clay bar soaps include wax, hydrogenated soybean oil (HSO), and various others. These hydrophobic ingredients impart moisture stability to the bar. They also have an effect on the lather profile of the bar by diminishing the quantity of lather that can be produced.

Palm Kernel Oil. In the first set, the effects of PKO were assessed. Upon evaluation of the samples, it is noted that the low concentration range of PKO in the formula (0.5-3 wt. %) gives negligible contributions to the overall water stability of the bar. Samples where PKO ranged from 0-3 wt. % (Samples DA-DE and EA-EE with all other ingredients held constant showed minimal differences in their dispersibility rates. Lather evaluation showed the opposite as an increase in PKO content simultaneously decreased lather generation and quantity.

Fatty Alcohols. Various fatty alcohols were substituted in the formulation for the PKO to assess the change.

Behenyl Alcohol (C22 alcohol) Differences between the control bar without behenyl alcohol and the bars with varying concentrations of behenyl alcohol were small for the dispersibility experiment. The bars with behenyl alcohol took longer to fully disintegrate in the test in comparison with the control. These results indicate that behenyl alcohol only makes a small impact on the water stability of the bar. It is noted that this result comes from the presence of 5 wt % wax, which has been shown in previous experiments to sufficiently impart high hydrophobicity to the bar on its own.

It is likely that the behenyl alcohol does give a beneficial contribution to the water stability but not to the extent of the wax's contribution.

For lather properties, it is noted that lather quantity and generation were not noticeably affected with the addition of behenyl alcohol. Quality of the lather, in contrast, was found to be improved-similar to the effect of adding small amounts of free fatty acid. The lather in the behenyl alcohol containing samples was noticeably creamier and thicker albeit with smaller bubbles than that without the fatty alcohol.

Behenyl Alcohol w/o Wax Included. Due to the heavy influence on the water stability properties of the bar due to the wax, formulas were evaluated with varying behenyl alcohol concentration in the absence of wax. Samples were made where the concentration of the behenyl alcohol was varied between 0-4 weight %.

From dispersion tests, it was confirmed that behenyl alcohol imparts noticeable hydrophobic character to the bar. Although not to the extent of waxes, it is noted that it has approximately equivalent properties to that of palm kernel oil in terms of increasing bar water stability. Also, the lather quantity is found to be only minimally reduced with increasing alcohol concentration, up to 4 wt %.

These findings indicate that fatty alcohols are viable materials to utilize as co-binding agents to help improve the use-up rate and slough issues.

The following materials are used in the following examples:

Fillers

| Manufacturer | Product Name | Type |
| --- | --- | --- |
| KaMin Performance Minerals | Polygloss ™ 90 | Kaolin |
| KaMin Performance Minerals | KaMin ™ HG90 | Kaolin |
| Barretts Minerals, Inc. | Talc | Talc |
| Argiletz S. A. | Kaolinite White Clay | Kaolin |

Surfactants

| Manufaturer | Product Name |
| --- | --- |
| Clariant | Cocoamidopropyl Betaine (CAPB) |
| Clariant | Hostapon ™ SCI-65 |
| Cognis | Comperlan ™ 100 (CMEA) |
| Stepan Chemicals Co. | Steol ™ OS-270 (SLES, 70%) |
| Finetex Inc. | Tauronol ™ SCMI-85 |
| BASF | Pluronic ™ F108 |
| Stepan Chemicals Co. | Stepanol ™ WA-10 NF/USP (SLS) |

Waxes and Oils

| Manufacturer | Product Name |
| --- | --- |
| Acidchem Intl. | Palmac ™ 98-12 |
| Croda | Syncrowax ™ HRC |
| Croda | Syncrowax ™ HGL-C |
| Cargill | RBD Palm Kernel Oil |
| Cargill | Hydrogenated Soybean Oil |
| Honeywell | Asensa ™ PR210 |
| Honeywell | Asensa ™ CL300 |
| Strahl & Pitsch, Inc. | White Ozokerite Wax |
| Strahl & Pitsch, Inc. | Microcrystalline Wax |
| Strahl & Pitsch, Inc. | Paraffin Wax |
| Strahl & Pitsch, Inc. | Beeswax |
| Strahl & Pitsch, Inc. | Ceresine Wax |

Additives and Miscellaneous

| Manufacturer | Product Name |
| --- | --- |
| Croda | Crodamol MM (Myristyl Myristate) |
| BASF Co. | Titanium Dioxide |
| Acidchem Intl. | Glycerin |
| Dow Chemical Co. | Polyox ™ WSR-N750 PEG-7M |
| ISP | Ceraphyl ™ 65 |
| Athena Environmental Sciences | MagiGlue ™ |
| Eastman | AQ 38S |
| Celanese | Celvol ™ 305 |

The following procedures are used to make the examples:
1. Lab Scale
    1.1 Weigh out formula amounts of the meltable ingredients in a mortar and heat to ~60-80° C. to melt. Maintain this elevated temperature throughout preparation process. Mix well with pestle until molten liquid is homogenous. Meltable ingredients include:
        a.) Sodium Cocoyl Isethionate (SCI, SCI-65, etc.)
        b.) Coconut Fatty Acid Monoethanolamide (CMEA)
        c.) Any fatty acids/oils—Palm Kernel Oil (PKO), Hydrogenated Soybean Oil (H-Soy), etc.
        d.) Wax—Ceresin, White Ozokerite, Polyethylene (Asensa™ PR210), etc.
    1.2 Weigh out formula amounts of Talc and other non-soluble solid additives. Add the weighed materials to the molten liquid prepared previously and mix well with pestle until homogenous. Non-soluble solid additives may include:
        a.) Polyox™ WSR N-750
        b.) Titanium Dioxide (TiO$_2$)
    1.3 Weigh out formula amount of clay and add to the doughy liquid mixture formed in previous step. Mix the clay into the mixture vigorously with pestle for at least 10 minutes until homogenous composition is attained.
    1.4 Add in measured formula amounts of liquid surfactant and other room temperature liquids to the dough formed in previous stage. Mix rigorously again until homogenous. Liquids added in this stage include:
        a.) 70% Sodium Laureth Sulfate (SLES-3EO)
        b.) 30% Cocoamidopropyl Betaine (CAPB)
        c.) Glycerin
        d.) DI Water
    1.5 Once dough-like mixture is mixed thoroughly, press into miniature bar shape using hands.
2. Pilot Plant Scale
    2.1 Weigh out formula amounts of the meltable ingredients a large 2 liter mortar and heat to ~60-80° C. using hot plate to melt. Maintain this elevated temperature throughout preparation process. Mix well. Meltable ingredients include:
        a.) Sodium Cocoyl Isethionate (SCI, SCI-65, etc.)
        b.) Coconut Fatty Acid Monoethanolamide (CMEA)
        c.) Any fatty acids/oils—Palm Kernel Oil (PKO), Hydrogenated Soybean Oil (H-Soy), etc.
        d.) Wax—Ceresin, White Ozokerite, Polyethylene (Asensa PR210), etc.

2.2 Weigh out formula amounts of filler material (i.e. clay and talc) and other non-soluble solid additives. Add the weighed materials to the molten liquid prepared previously and mix well with pestle. Non-soluble solid additives may include:
 a.) Polyox™ WSR N-750
 b.) Titanium Dioxide (TiO$_2$)
2.3 Add in measured formula amounts of liquid surfactant and other room temperature liquids to the dough formed in previous stage. Mix rigorously again until homogenous. Liquids added in this stage include:
 a.) 70% Sodium Laureth Sulfate (SLES-3EO)
 b.) 30% Cocoamidopropyl Betaine (CAPB)
 c.) Glycerin
 d.) DI Water
2.4 Once dough-like mixture is mixed thoroughly, send the material through the extruder to create billets.
2.5 Press the billets using the soap press to create bars.

The following formulations are made using the procedures above:

| Ingredients | D1 wt % | D2 wt % | D3 wt % |
|---|---|---|---|
| Polygloss 90 | 50 | 60 | 60 |
| Paraffin Wax | 50 | 22 | 12 |
| Myristyl Myristate | 0 | 5 | 4 |
| 70% SLES | 0 | 11 | 20 |
| Pluronic™ F108 | 0 | 1.50 | 3 |
| CMEA | 0 | 0.50 | 1 |
| Σ | 100 | 100 | 100 |

Formulations for Lab Scale Batch Preparation Assessments

| Ingredients | D4 wt. % | D5 wt. % | D6 wt. % |
|---|---|---|---|
| Polygloss™ 90 | 60 | 60 | 60 |
| Paraffin Wax | 22 | 22 | 22 |
| SCMI-85 | 0 | 0 | 16 |
| 70% SLES | 16 | 16 | 0 |
| Pluronic™ F108 | 1.5 | 1.5 | 1.5 |
| CMEA | 0.5 | 0.5 | 0.5 |
| Σ | 100 | 100 | 100 |

Formulations for Filler Assessment

| Ingredients | D7 wt. % | D8 wt. % | Ingredients | D9 wt. % | D10 wt. % |
|---|---|---|---|---|---|
| Polygloss™ 90 | 45 | 0 | Talc | 65 | 62 |
| Talc | 20 | 65 | Ceresine Wax | 15 | 10.50 |
| Polyox™ WSR N-750 | 1 | 1 | CFA | 0 | 4.50 |
| Ceresine Wax | 15 | 15 | Ceraphyl™ 65 | 0 | 0 |
| Paraffin Wax | 0 | 0 | 70% SLES | 16 | 16 |
| SCMI-85 | 16 | 16 | CMEA | 1 | 3 |
| 70% SLES | 0 | 0 | Polyox™ WSR N-750 | 1 | 0 |
| Pluronic F108 | 0 | 0 | Glycerin | 2 | 2 |
| CMEA | 3 | 3 | DI Water | 0 | 2 |
| Σ | 100 | 100 | Σ | 100 | 100 |

Formulations for Wax Type Studies

| Ingredient | D11 wt % | D12 wt % | D13 wt % | D14 wt % | D15 wt % | D16 wt % | D17 wt % |
|---|---|---|---|---|---|---|---|
| KaMin™ HG90 | 50 | 50 | 50 | 50 | 50 | 50 | 50 |
| Talc | 15 | 15 | 15 | 15 | 15 | 15 | 15 |
| Glycerin | 2 | 2 | 2 | 2 | 2 | 2 | 2 |
| White Ozokerite Wax | 5 | 0 | 0 | 0 | 0 | 0 | 0 |
| Microcrystalline Wax | 0 | 5 | 0 | 0 | 0 | 0 | 0 |
| Paraffin Wax | 0 | 0 | 5 | 0 | 0 | 0 | 0 |
| Asensa™ PR210 | 0 | 0 | 0 | 5 | 0 | 0 | 0 |
| Asensa™ CL300 | 0 | 0 | 0 | 0 | 5 | 0 | 0 |
| H-Soybean Oil | 0 | 0 | 0 | 0 | 0 | 5 | 0 |
| Syncrowax™ HGL-C | 0 | 0 | 0 | 0 | 0 | 0 | 5 |
| Palmac™ 98-12 | 1 | 1 | 1 | 1 | 1 | 1 | 1 |
| 70% SLES-3EO | 9 | 9 | 9 | 9 | 9 | 9 | 9 |
| SCI-65 | 4 | 4 | 4 | 4 | 4 | 4 | 4 |
| CMEA | 2 | 2 | 2 | 2 | 2 | 2 | 2 |
| DI Water | 12 | 12 | 12 | 12 | 12 | 12 | 12 |
| Total | 100.0 | 100.0 | 100.0 | 100.0 | 100.0 | 100.0 | 100.0 |

Formulations for Surfactant Assessment

| Ingredient | D11 wt % | D12 wt % | D13 wt % | D14 wt % | D15 wt % | D16 wt % | D17 wt % | D18 wt % | D19 wt % | D20 wt % |
|---|---|---|---|---|---|---|---|---|---|---|
| KaMin™ HG90 | 50 | 50 | 50 | 50 | 50 | 50 | 50 | 50 | 50 | 50 |
| Talc | 17 | 15 | 13 | 15 | 13 | 17 | 15 | 13 | 15 | 13 |
| Glycerin | 2 | 2 | 2 | 2 | 2 | 2 | 2 | 2 | 2 | 2 |
| Ceresine Wax | 3 | 3 | 3 | 5 | 5 | 3 | 3 | 3 | 5 | 5 |
| Palmac™ 98-12 | 1 | 3 | 5 | 1 | 3 | 1 | 3 | 5 | 1 | 3 |
| 70% SLES-3EO | 9 | 9 | 9 | 9 | 9 | 12 | 12 | 12 | 12 | 12 |
| SCI-65 | 4 | 4 | 4 | 4 | 4 | 5 | 5 | 5 | 5 | 5 |
| CMEA | 2 | 2 | 2 | 2 | 2 | 3 | 3 | 3 | 3 | 3 |
| DI Water | 12 | 12 | 12 | 12 | 12 | 7 | 7 | 7 | 7 | 7 |
| Total | 100 | 100 | 100 | 100 | 100 | 100 | 100 | 100 | 100 | 100 |

Hydrogenated Soybean Oil Based Clay Bar Formulations

| Ingredients | E1 wt % | E2 wt % |
|---|---|---|
| Kaolin White Clay | 50.47 | 50 |
| Talc | 13.03 | 12.50 |
| Glycerin | 2.44 | 1 |
| SLES, 70% | 8.14 | 12 |
| Polyox ™ WSR N-750 | 0.33 | 0.30 |
| Tap Water | 14.81 | 12.20 |
| Sodium Cocoyl Isethionate | 5.70 | 3 |
| CMEA Flake | 0 | 2 |
| Hydrogenated Soybean Oil | 5.08 | 2.50 |
| RBD PKO | — | 4.50 |
| Total | 100 | 100 |

Formulations for Pilot Plant Studies

| Ingredients | F1 wt % | F2 wt % | F3 wt % | F4 wt % | F5 wt % |
|---|---|---|---|---|---|
| KaMin ™ HG90 | — | — | 54.5 | 25 | 45 |
| Talc | 62 | 65 | 13.6 | 40 | 20 |
| Ceresine Wax | 10 | 3 | 2.7 | 3 | 5 |
| Palmac ™ 98/12 | 0 | 2 | 1.8 | 2 | 2 |
| 70% SLES-3EO | 13 | 12 | 10.9 | 12 | 12 |
| CMEA | 0 | 3 | 2.7 | 3 | 2 |
| CAPB | 8 | 5 | 4.5 | 5 | 4 |
| SCI-65 | 5 | 8 | 7.3 | 8 | 8 |
| Glycerin | 2 | 2 | 2 | 2 | 2 |
| Σ | 100 | 100 | 100 | 100 | 100 |

Additional Examples Incorporating the Wax/Clay Bar

The following are additional results obtained from preliminary trials incorporating the wax-clay bar.

a.) Lather

| | D1* | D2 | D3 |
|---|---|---|---|
| Generation | n/a | None | Fast |
| Amount | n/a | None | moderate-high |
| Quality | n/a | None | large bubbles, non-creamy |
| Post-Wash Skin Feel | n/a | greasy, waxy | soft, but noticeable stickiness to skin after wash |

*No surfactants were added to this sample b.) Dispersibility

| | D1 | D2 | D3 |
|---|---|---|---|
| initial | 0 | 0 | 0 |
| 30 min | 0 | 1 | 1 |
| 1 hr | 0 | 1 | 5 |
| 2 hrs | 0 | 3 | 20 |
| 3 hrs | 0 | 5 | >50 |
| 1 day | 0 | 10 | 100 |
| 3 days | 0 | >50 | — |

Data represents approximate loss in wt. %

In this example, it is observed that it is quite feasible to incorporate wax into the clay without the use of emulsifiers. The wax readily adsorbs onto the clay surface and simply requires mixing to cover the clay's surface with wax. The ingredients used in the above example have highly diverging properties, coupled with the application of heat needed to prepare the sample that makes homogenization a challenge. However, this obstacle was overcome by vigorous mixing while maintaining the elevated temperature of the mortar throughout the process.

Sample D2 possesses high concentrations of wax that completely eliminates the bar's ability to generate foam. It is theorized that large concentrations of surfactants, in sample D3, allow for the product to generate a sufficient amount of foam comparable to regular soap bars at the expense of the bar's stability in a wet environment. It is contemplated that in order to create viable formulations, that there must be an optimal balance between the surfactant and wax content.

The following are results obtained from the Lab Scale Batch Preparation Assessments.

Of note, only the preparation of compound D4 varies from the above procedure, which is used to produce the lab scale batch preparations used to produce the examples herein. This procedure deviates from the protocol described above, used to produce the examples disclosed herein in that the surfactant and other liquids are added to the molten meltables prior to adding the filler material. However, this procedure is identical in the other steps.

a.) Lather Assessment:

| | D4 | D5 | D6 |
|---|---|---|---|
| Generation* | Slow | Parity | Slow |
| Amount | Moderate | Moderate | Low-moderate |
| Quality | Loose, thin medium sized bubbles | Loose, thin, large bubbles | Creamy, small bubbles |
| Post-Wash Skin Feel | Draggy skin feel when skin is still wet, clean skin feel when dry | Identical to D4, slightly more clean feeling | Draggy skin feel when skin is still wet, smooth skin feel when dry |

*In comparision Palmolive bar soap b.) Dispersibility Assessment:

| | D4 | D5 | D6 |
|---|---|---|---|
| initial | 0 | 0 | 0 |
| 30 min | trace | 1 | trace |
| 1 hr | 1 | 2 | 1 |
| 2 hrs | 2 | 2 | 2 |
| 3 hrs | 3 | 3 | 5 |
| 1 day | 5 | 5 | 10 |
| 3 days | >50 | >50 | >50 |

Data represents approximate loss in wt. %

In this example, the order of addition of ingredients affects the final properties of the bar. For example, adding surfactant after the clay has absorbed the wax increases lather properties between the variations of preparation. Without being bound to any particular theory, it is believed that this is most likely due to fuller adsorption of the hydrophobic wax by the filler and lesser interaction between the surfactant and wax. Of note, that at this high concentration of wax, the change in order of addition of ingredients did not significantly impact the dispersibility of the prototypes.

In one aspect of the invention, sodium cocoyl methyl isethionate (SCMI) and sodium laureth sulfate (SLES) are both contemplated as being the primary surfactant in the composition. SCMI gives a less irritating and creamier lather in comparison with SLES. However, the lather of SLES based prototypes are superior in terms of volume and quickness of lather. This result is expected due to the nature of the two types of surfactants.

The following are results obtained from the initial formulation work used to produce the examples discussed herein.

In this work, the ranges of the ingredients noted above are varied in order to find optimal ratios of ingredients for further refinement. Different types of filler, wax, and surfactants are also assessed as to their performance in the wax-clay bar system.

a.) Lather

|  | D7 | D8 | D9 | D10 |
|---|---|---|---|---|
| Generation* | Parity | Parity | Slightly faster | Fast |
| Amount | Low-moderate | Low | Moderate | Low-moderate |
| Quality | Creamy, small bubbles | Creamy, small bubbles | Large bubbles initially, but quickly dissipates | Medium sized bubbles, quickly dissipates |
| Post-Wash Skin Feel | Moderate drag sensation, clean dry skin feel | Slight drag sensation, clean dry skin feel | Slight drag sensation, clean dry skin feel | Very slight drag sensation, very soft and clean skin feel |

*In comparison Palmolive is bar soap b.) Dispersibility

|  | D7 | D8 | D9 | D10 |
|---|---|---|---|---|
| initial | 0 | 0 | 0 | 0 |
| 30 min | trace | trace | trace | 2 |
| 1 hr | 1 | trace | 1 | 3 |
| 2 hrs | 2 | 1 | 2 | 5 |
| 3 hrs | 5 | 2 | 5 | 10 |
| 1 day | 20 | 10 | 10 | 30 |

Similar to other examples disclosed herein, regarding lathering properties, the samples containing talc had a diminished lather profile in relation to solely kaolin based bars. For example, one may compare the lather profiles of samples D5 (from previous experiment) and D9, which have nearly identical surfactant composition, but differ in type of filler. In comparison with the prototypes made in the previous examples, without talc and Polyox™, the bars made in this experiment dramatically decreased in the amount of drag and stickiness felt by the skin after washing. Looking at the properties of talc, it is observed that it is actually a slightly hydrophobic and very lipophillic type of clay. It is theorized that the talc plays a role in the decrease in wax dispensed on the skin to wax being adsorbed.

For the dispersibility characteristics, in samples containing the same amount of wax, the use of talc improves the stability of the bar in water. From the results, it is noted that the effect of talc on the dispersion rate of the bar is not as significant as that of the wax and surfactant composition. Nevertheless, talc can still aid in the balancing of the latter two ingredients in the formula for optimum dispersion characteristics.

It is also noted that the use of solely talc in the bar causes an undesirable softening of the bar in comparison to kaolin containing samples. Structure and lipophilic/hydrophilic differences between kaolin and talc are theorized to be attributed to this trend. In combining the results of these trials, we understand that there has to be a balance between kaolin and talc for optimum physical and performance properties.

Initial Formulation Work and Wax Type Assessment.

One property of the wax-clay bar is the noticeable drag felt on the skin after washing with the bars. For example, soap bars are usually concomitant with a very "squeaky clean feeling," as said by several panelists whom tested the compounds of the examples disclosed herein. Thus, it can be said that traditional soap bars possess less noticeable drag. The drag sensation is attributed to the wax. This effect is seen when comparing samples with and without wax with otherwise identical composition. In at least one aspect of the present invention it is desirable to achieve a "soap-like" product that possesses little or no drag sensation. Thus, it is contemplated that it is desirable to achieve an optimum range of wax content wherein there is sufficient wax to impart hydrophobicity to the clay bars without leaving the aforementioned drag sensation.

In total wax content studies, the total wax content is varied in the wax-clay bars from 2 to 20 wt %. The table below presents the dispersability data obtained from this experimentation. All samples contained 15-16% SLES, 50% kaolin, and 15% talc.

|  | Wax % | | | | | |
|---|---|---|---|---|---|---|
| Time (min) | 20% N3 % disp. | 15% N2 % disp. | 12% N4 % disp. | 10% N1 % disp. | 3% N5 % disp. | 2% N6 % disp. |
| 0 | 0 | 0 | 0 | 0 | 0.5 | 0.5 |
| 30 | 0.5 | 0.5 | 0.5 | 1 | 3 | 3 |
| 60 | 1 | 0.5 | 1 | 2 | 7 | 7 |
| 90 | 1 | 1 | 2 | 3 | 10 | 10 |
| 120 | 2 | 2 | 3 | 5 | 30 | 30 |
| 180 | 5 | 5 | 5 | 10 | 50 | 70 |
| 1440 | 6 | 10 | 15 | 15 | 100 | 100 |

The data in the table above shows that with ≥10% wax content, the bars are highly water stable and there is little performance enhancement with increasing wax content. Moreover, from the data of the 2-5% samples, it was observed that the dispersion rates are relatively the same for the first 90 minutes before they begin to deviate. It is theorized that this latter observation was due to the time it takes for water to penetrate the inner parts of the bar, which, in turn, increases the surface area the water has to disperse the bar.

In this example, there was an attempt to determine quantitative data for the amount of wax deposited on the skin from the wax-clay bars. This quantitative assessment is ultimately accomplished by use of a panel of group members to qualitatively assess the drag sensation from each bar. Panelists are then asked to hand wash with each bar. Palmolive bar soap was used in between each washing to remove the wax deposition from the trial samples. A positive correlation is observed between total wax content and that drag sensation which the panelists experience.

Initial Formulation Work and Wax Type Studies.

In this example, 6 different waxes and hydrogenated soybean oil (HSO) are screened in the wax-clay bar system. The samples are prepared with identical composition other than wax type. The samples contained 5% of the wax, 50/15% of kaolin/talc, and 15% total surfactants.

In terms of dispersibility, all of the samples display almost equal performance, except for the HSO based sample, which fully disintegrates within 2 hours. This result is expected, since HSO is more easily emulsified by the surfactants, thus negating its contribution to the hydrophobicity of the bar.

The same panelists that took part in the assessment of total wax content were asked to assess any differences in terms of drag sensation from the bars. Responses were highly varied, however two samples containing White Ozokerite wax (a wax mixture from Strahl & Pitsch) and polyethylene wax (Asensa™ PR210 from Honeywell), respectively, were found to give the least drag sensation.

Initial Formulation Work and Surfactant Assessment

As noted before in the preliminary trials of the wax-clay bar, surfactant composition contributes considerably to the dispersion rate and consequently the water stability of the bar in addition to being the cleansing agent in the system. Here, various surfactant combinations known to be effective as well as total surfactant loads are screened. Several additives may be employed to explore their uses in enhancing the lather profile of the wax-clay bar system.

From previous experimentation, it was known that samples containing less than 12% total surfactants produced little to no lather and samples containing >20% total surfactants severely diminished the clay bar's stability in water. For purposes of this example, total surfactant loads of 15% and 20% were used with consistent ratios of the types of surfactants used. The surfactant system that has proven to work very well from the previous experiments is the SLES/SCI/CMEA combination at approximately 4:2:1 ratio, respectively. It was learned from previous experimentation that the rest of the formulation, especially in the case of fatty acids, oils, and waxes, affected the lather profile. The variation of the samples was done by changing the wax/fatty acid ratio and content on both the 15% and 20% total surfactant samples. The following data table compares the lather performance of the samples in relation to Palmolive bar soap. The dispersibility results of the samples are also presented with a control sample of Palmolive bar soap.

| Sample | Total Composition Percentage | | | Lather | | |
|---|---|---|---|---|---|---|
| | Wax | Fatty Acids | Surfactants | generation | quantity | quality |
| G1 | 3 | 1 | 15 | + | = | = |
| G2 | 3 | 3 | 15 | + | = | + |
| G3 | 3 | 5 | 15 | − | − | = |
| G4 | 5 | 1 | 15 | + | − | = |
| G5 | 5 | 3 | 15 | = | − | − |
| G6 | 3 | 1 | 20 | ++ | + | + |
| G7 | 3 | 3 | 20 | + | = | + |
| G8 | 3 | 5 | 20 | − | − | = |
| G9 | 5 | 1 | 20 | + | + | + |
| G10 | 5 | 3 | 20 | + | = | + |

Legend: "+" better performance; "=" parity performance; "−"worse performance

The table below notes the dispersion rates of the above tested compounds.

From the results, it was noted immediately that performance of the bars can vary dramatically with the change in amount of free fatty acid (Palmac™ 98-12; $C_{12}$ fatty acid) added. With increasing fatty acid concentration, the bar became increasingly more water stable. However, there was an associated dramatic decrease in lather quantity of the bars. From these results, we theorize that the fatty acid works to increase the stability of the bar in water by interacting with the surfactants and limiting the extent of the surfactant-water interaction when submerged in water. The fact that there is a dramatic decrease in foam generation with increasing fatty acid concentration helps support this theory, for example.

In comparing the effect of total surfactant percentage, it is observed that with balanced levels of fatty acid and wax, 15% total surfactants can perform on parity or with superior lather properties than that of the Palmolive bar soap (samples G1 & G2). Samples with 20% total surfactants have superior lather attributes except for the sample containing 5% fatty acid. However, samples with 20% surfactants are significantly less stable in water than samples containing only 15% surfactants.

It is noted that HSO performs very well in structurally binding the clay bar system without giving adverse effects on the lather profile of the bar. However, the bar still suffers from significant soap slough formation when left in a moist soap dish. From the results of prior work, it was decided upon to use wax to improve the bar's stability in wet environments. Thus, two types of exemplification exist. Those examples that possess formulations that avoid using wax to minimize processing difficulties and those examples that employ wax to explore the benefits of wax inclusion.

Wax and Hydrogenated Soybean Oil Clay Bars. From the wax assessment of previous work, it was observed that White Ozokerite wax and polyethylene wax (Asensa™ PR210) gave the lowest side effect of the "drag" and "sticky" skin feel after washing. Wax content was varied from 2-8 wt. % and was added to the best HSO prototype—E2.

The addition of wax into the bar substantially improved the dispersibility rate of the HSO-based bars in comparison with Sample E2. Both types of waxes are similar in performance. The polyethylene wax did present significantly more issues on sample preparation due to its high melting point (~90 C) and rapid hardening. Qualitative lather assessment of the bars showed that the wax had a minor negative impact on generation and quality of lather.

The table below notes the dispersion rates of the wax and hydrogenated soybean oil clay bars of the examples disclosed herein.

| | Sample | | | | | | | | | |
|---|---|---|---|---|---|---|---|---|---|---|
| Time | G1 % disp. | G2 % disp. | G3 % disp. | G4 % disp. | G5 % disp. | G6 % disp. | G7 % disp. | G8 % disp. | G9 % disp. | G10 % disp. |
| 0 | 1 | 0 | 0 | 0 | 0 | 1 | 1 | 0 | 0 | 0 |
| 30 | 30 | 10 | 1 | 20 | 1 | 20 | 20 | 5 | 20 | 10 |
| 60 | 50 | 15 | 5 | 30 | 5 | 50 | 30 | 5 | 40 | 30 |
| 90 | 80 | 30 | 8 | 50 | 8 | 80 | 50 | 10 | 50 | 45 |
| 120 | 100 | 40 | 10 | 100 | 10 | 100 | 100 | 20 | 100 | 60 |
| 180 | 100 | 60 | 15 | 100 | 20 | 100 | 100 | 40 | 100 | 80 |

| Time (min) | 0% Standard % disp. | 0% E2 % disp. | Wax % 20% M1 % disp. | 15% M2 % disp. | 12% M3 % disp. | 10% M4 % disp. | 3% M5 % disp. | 2% M6 % disp. |
|---|---|---|---|---|---|---|---|---|
| 0 | 0 | 1 | 1 | 1 | 1 | 1 | 1 | 1 |
| 30 | 0 | 10 | 10 | 3 | 3 | 10 | 3 | 1 |
| 60 | 2 | 30 | 10 | 5 | 5 | 15 | 5 | 5 |
| 90 | 5 | 50 | 15 | 12 | 10 | 20 | 15 | 10 |
| 120 | 8 | 80 | 40 | 15 | 15 | 30 | 20 | 20 |
| 180 | 10 | 100 | 50 | 30 | 20 | 50 | 30 | 30 |
| 240 | 13 | 100 | 60 | 50 | 30 | 80 | 50 | 50 |

Pilot Plant Studies.

The physical properties of the processed bars on the pilot plant scale are noticeably different than those made in the lab.

Hardness of the bars was one of the first attributes found to be noticeably different between samples made on the lab scale versus those made on the pilot plant scale. To adjust hardness of the bar, both water content and filler were adjusted. During large scale mixing, the mixing times were extended to ensure homogeneity of the batch. Much of the water content contributed by the SLES is evaporated during this extended mixing period, thus extra water is required to replace the amount evaporated. It should be noted that the amount of extra water necessary varies greatly, depending both on the formulation and mixing parameters. In general, the lesser the total surfactant and wax/HSO used, the more water needed. Filler ratio of clay talc to give optimal hardness at approximately 10:3 ratio, resulting in 50/15 wt. % in the final formulation. In the event too much talc is added, the bars become too soft which results in a highly brittle bar.

The pilot plant scale bars also had the tendency to crack and form fissures around the perimeter of the bar, wherein the top and bottom of the soap press forms an edge on the bar. Fissures are problematic as they lead to excess water penetration and the bar disperses more rapidly. However, this problem may be overcome by adding small amounts of palm kernel oil in addition to HSO eliminated this problem.

Moisturization Studies. Moisture efficacy of the HSO and wax formulation is determined via testing the clay bar against a common Palmolive™ bar of soap while varying the amount of surfactant in each clay bar of soap. Pigskin moisturization studies were conducted on the following samples: G1 (contains 15% surfactants); G2 (contains 20% surfactants); E1; and Control (Palmolive Brand bar soap).

The table below illustrates that the formulas of the examples disclosed herein remain better than regular toilet soaps. Although sample G2 only had a minor improvement in moisturization in comparison to the control bar soap. It is theorized that this may be attributed to the large amount of surfactants used in the formula, which has been found to be a detriment to the water stability of the formulation.

| Sample | Moisturization Level |
|---|---|
| Control | 35 |
| E1 | 39 |
| G1 | 49 |
| G6 | 38 |

Hydrophobic Ingredient Assessments. Hydrophobic ingredients currently employed in the clay bar soaps include wax, hydrogenated soybean oil (HSO), and various others. These hydrophobic ingredients impart high moisture stability to the bar. They may also affect the lather profile of the bar by diminishing the quantity of lather that can be produced. Therefore, their inclusion requires a delicate balancing. Therefore, formulations varying the hydrophobic components have been prepared and assessed for their lather profile and dispersibility rates.

Palm kernel oil ("PKO"). The effects of PKO were assessed in the first set of experiments. Among those characteristics tested were: stability, dispersability, and lather analysis.

Upon evaluation of the samples, it was found that the low concentration range of PKO in the tested formula (0.5-3.0 wt. %) gave negligible contributions to the overall water stability of the bar. Indeed, samples where PKO ranged from 0-3.0 wt. % with all other ingredients held constant, showed minimal differences in their dispersibility rates. However, lather evaluation showed the opposite wherein an increase in PKO content simultaneously decreased lather generation and quantity of the trial samples.

Fatty alcohols. Fatty alcohols proved to be good agents in reducing the use-up rate of the bars without dramatic drawbacks on the lather and aesthetics.

Behenyl Alcohol. Behenyl alcohol allows easier preparation of soap bars when compared to those bars prepared without the use of behenyl alcohol. Without being bound to any particular theory, it is believed that the ease of preparation was due to the relatively low melting point of behenyl alcohol (~70° C.).

Differences between the control bar without behenyl alcohol, and those bars with varying concentrations of behenyl alcohol, are small with regards to dispersability. Although, the bars with behenyl alcohol take longer to fully disintegrate in the test in comparison to the control. Thus, these results indicate that behenyl alcohol only makes a small impact on the water stability of the bar. It is theorized that the reason for the differences in stability is believed to arise from the presence of 5 wt % wax. In other studies, the presence of wax has been shown to sufficiently impart high hydrophobicity to the bar on its own. It believed that while the presence of behenyl alcohol gives a beneficial contribution to the water stability that it in fact pales in comparison to the impact on stability due to the presence of the wax.

It was observed that lather quantity and generation were not noticeably affected by the addition of behenyl alcohol. However, lather quality was improved. This effect was similar to the effect seen from adding small amounts of free fatty acid. The lather in the behenyl alcohol containing samples was noticeably creamier and thicker albeit with smaller bubbles than that without the fatty alcohol.

Behenyl alcohol without wax included. Due to the heavy influence on the water stability properties of the bar due to the wax, formulas with varying behenyl alcohol concentration in the absence of wax were evaluated. Samples of behenyl alcohol tested varied between concentrations 0-4%.

Dispersion tests confirm that behenyl alcohol imparts a noticeable hydrophobic character to the bar. This hydrophobic effect is not as great as the effect previously observed by the inclusion of waxes. However, it was found to have approximately equivalent properties to that observed by the addition of PKO, regarding the increasing bar water stability. Moreover, the lather quantity was observed to be only minimally reduced with increasing alcohol concentration. This minimal reduction is seen up to 4 wt %.

These observed findings indicate that fatty alcohols are viable materials to utilize as co-binding agents to help improve the use-up rate and slough issues that are observed without the inclusion of a co-binding agent.

Performacol 350 and Performacol 425. To evaluate the effects of increasing the chain length of the fatty alcohol on the clay bar, we evaluated 2 longer chain mixtures of fatty alcohols from New Phase Technologies. The melting points of Performacol 350 and Performacol 425 are 85° C. and 92° C. respectively.

These fatty alcohols presented an issue when preparing in the lab scale. Since their melting points were so high, the mixtures had to be heated to high temperatures to mix everything together. The resulting dough became very sticky and hardened as soon as it was removed from the mortar and pestle, making the molding step very difficult. Due to this, yield was very low and the bars were not fully homogenous and had fissures throughout due to hardening of the surfaces.

Dispersibility of these bars show that they have approximately the same or in some cases less water stability properties than that of behenyl alcohol. This observation is possibly attributed to the higher surface area that water has to penetrate the bar, since the bars were imperfect. The lather profiles of the bars were found to be equivalent to those made with behenyl alcohol.

Preparation of Clay Bars on the Kilogram and Above Scale.

The following materials were used in the following examples:

| KaMin HG90 Talc | SLES, 70% Hostapon™ SCI-65 | Behenyl Alcohol Stearyl Alcohol | TiO2 80/20/1 Soap Chip (SBSC) |
|---|---|---|---|
| Glycerin | Comperlan™ 100 CMEA | Cetyl Alcohol | Microcrystalline Wax |
| Hydrogenated Soybean Oil | White Ozokerite Wax | Synthetic Beeswax | Polyox™ WSR-N 750 |
| Polawax | Ceresin Wax | Paraffin Wax (SP434) | Wellness 155936 E |

Batch Preparation Procedure.

In the following examples, the equipment that is evaluated is known as the Varimixer; this piece of equipment is an industrial food mixer obtained from E.A. Supply. A heating jacket with controllable thermostat is wrapped around the Varimixer's mixing bowl, allowing for controlled heating conditions. The Varimixer also has variable mixing speeds, allowing for controlled mixing. A simplex extruder (those traditionally used to extrude slugs of soap) is then used to refine and extrude the clay bar 'chip' into billets for stamping on a soap press.

The following procedures are used in the following examples:

1. The Varimixer mixing bowl is warmed up and kept heated using a heating mantle with the rheostat set at 80.
2. Meltable ingredients are weighed out, added into the Varimixer, and mixed at speed setting 1.0 until ingredients are melted.
3. Talc is added into the melt and the mixing speed is increased to 2.0 until the mixture is homogenous. (approx. 10 minutes)
4. Kaolin and other particulates are slowly added into the mixture, with continued mixing at 2.0 setting. (approx. 15-20 minutes)
5. Liquid ingredients are then weighed and added into the mixture, with mixing speed increased to 2.5-3.0 setting. Mixing is done until the dough is sufficiently homogenous. (approx. 10-15 minutes)
6. The heating mantle is removed from the Varimixer™ mixing bowl, and mixing is continued for another 3-5 minutes until it has cooled sufficiently to handle by hand.
7. The dough is then extruded 3 times and any extra water is added during this stage.
8. The extruded dough is then made into billets and pressed into bar shape.

An issue arising from the Varimixer is the fact that it is not an efficient mixer compared to other heavy duty manufacturing mixers, e.g. a sigma blade mixer. This results in occasional grainy material in the final dough mixture. Analysis confirms that the grains are unbroken pieces of SCI and/or re-solidified wax. The best means to eliminate the former is to extend mixing times, especially the step in which the talc is being mixed in with the meltables. As for the latter, the wax re-solidifies when cold or room temperature liquids are added into the mixture, of which can avoided by preheating the liquids in a hot water bath. Also, large concentrations of hydrophobics (e.g. >10% wax, fatty alcohol, etc.) result in an excessively sticky dough that impedes the collection of the finished dough mixture from the Varimixer.

Formulations for clay bars at kilogram or above scale. Wax screening Formulations are as Follows

| Ingredient | Sample | | | | | | |
|---|---|---|---|---|---|---|---|
|  | H1 wt % | H2 wt % | H3 wt % | H4 wt % | H5 wt % | H6 wt % | H7 wt % |
| KaMin™ HG90 | 50 | 50 | 50 | 50 | 50 | 50 | 50 |
| Talc | 15 | 15 | 15 | 15 | 15 | 15 | 15 |
| Glycerin | 1 | 1 | 1 | 1 | 1 | 1 | 1 |
| SLES, 70% | 12 | 12 | 12 | 12 | 12 | 12 | 12 |
| Hostapon™ SCI-65 | 3 | 3 | 3 | 3 | 3 | 3 | 3 |
| Comperlan™ 100 CMEA | 2 | 2 | 2 | 2 | 2 | 2 | 2 |
| Behenyl alcohol | 0 | 0 | 0 | 0 | 0 | 0 | 0 |
| Hydrogenated Soybean Oil | 4 | 4 | 4 | 4 | 4 | 4 | 4 |
| White Ozokerite Wax | 4 | 0 | 0 | 0 | 0 | 0 | 0 |
| Synthetic Beeswax | 0 | 4 | 0 | 0 | 0 | 0 | 0 |
| Paraffin Wax (SP434) | 0 | 0 | 4 | 0 | 0 | 0 | 0 |
| Microcrystalline Wax | 0 | 0 | 0 | 4 | 0 | 0 | 0 |
| Ceresin Wax | 0 | 0 | 0 | 0 | 4 | 6 | 8 |
| DI Water | 9 | 9 | 9 | 9 | 9 | 7 | 5 |
| Total | 100 | 100 | 100 | 100 | 100 | 100 | 100 |

Fatty Alcohol Screening Formulations

| Sample Ingredient | I1 wt % | I2 wt % | I3 wt % |
|---|---|---|---|
| KaMin™ HG90 | 50 | 50 | 50 |
| Talc | 15 | 15 | 15 |
| Glycerin | 1 | 1 | 1 |
| SLES, 70% | 12 | 12 | 12 |
| Hostapon SCI-65 | 3 | 3 | 3 |
| Comperlan™ 100 CMEA | 2 | 2 | 2 |
| Bohenyl Alcohol | 4 | 0 | 2 |
| Stearyl Alcohol | 0 | 4 | 0 |
| Cetyl Alcohol | 0 | 0 | 0 |
| Hydrogenated Soybean Oil | 4 | 4 | 4 |
| White Ozokerit Wax | 0 | 0 | 2 |
| Polyox™ WSR-N 750 | 0.5 | 0.5 | 0.5 |
| Di Water | 8.5 | 8.5 | 8.5 |
| Total | 100 | 100 | 100 |

Polawax Assessment Formulations

| Sample<br>Ingredient | J1<br>wt % | J2<br>wt % | J3<br>wt % |
|---|---|---|---|
| KaMin ™ HG90 | 50 | 50 | 50 |
| Talc | 15 | 15 | 15 |
| Glycerin | 1 | 1 | 1 |
| SLES, 70% | 12 | 12 | 14 |
| Hostapon ™ SCI-65 | 3 | 5 | 3 |
| Comperlan ™ 100 CMEA | 2 | 2 | 2 |
| Hydrogenated Soybean Oil | 4 | 4 | 4 |
| Polawax ™ | 4 | 2 | 2 |
| Polyox ™ WSR-N-750 | 0.5 | 0.5 | 0.5 |
| DI Water | 8.5 | 8.5 | 8.5 |
| Total | 100 | 100 | 100 |

Surfactant Reduction Trials

| | Sample | | |
|---|---|---|---|
| Ingredient | K1<br>wt % | K2<br>wt % | K3<br>wt % |
| KaMin ™ HG90 | 50 | 50 | 50 |
| Talc | 15 | 15 | 15 |
| Glycerin | 1 | 1 | 1 |
| SLES, 70% | 12 | 10 | 8 |
| Hostapon ™ SCI-65 | 3 | 2 | 2 |
| Comperlan ™ 100 CMEA | 2 | 2 | 2 |
| Behenyl Alcohol | 0 | 0 | 0 |
| Stearyl Alcohol | 4 | 4 | 4 |
| Cetyl Alcohol | 0 | 0 | 0 |
| Hydrogenated Soybean Oil | 4 | 4 | 4 |
| Ceresine Wax | 4 | 4 | 4 |
| Polyox ™ WSR-N 750 | 0 | 0 | 0 |
| DI Water | 5 | 8 | 10 |
| Total | 100 | 100 | 100 |

Methods for Evaluation of Clay Bars Produced at Kilogram or Above Scale.

Use-Up Rate Analysis. First, the dry bar was initially weighed. Next, the bar was rolled in the operator's hand for 10 sec in the presence of a gentle stream of ~38° C. (~100° F.) tap water. To insure consistency, washing is performed using one experimenter. Each ten-second wash is then separated by a 30 minute interval. The washings are repeated for a total 10 washes per day, to a total of 20 or 30 washes total. The bars are kept in soap dishes with drainage, to prevent slough (wet mush) from forming. After each wash was completed, the bars were allowed to air dry in the soap dishes and the post-wash mass was recorded. The use-up rate was then obtained via obtaining the difference in weights and then plotting this difference against the number of washes. The use-up rates for the clay bars were compared against that of the 85/15 toilet soap bar.

Slough formation assessment. Slough formation of the prototypes was conducted at room temperature (RT) and ambient humidity. Each bar is washed for 30 seconds under warm 35-38° C. (95-100° F.) running water. They are subsequently placed in a soap dish containing sufficient water (~35-40 mL) to submerge half of the bar. The bars are left submerged for 17-20 hours overnight and removed from the water the next day. The experimenter removes the softened "slough" or outer layer of the bar and allows it to dry over 2-3 days. The dried bar is weighed and the slough is calculated as a weight percent loss. In certain embodiments, the cleansing bar has a slough (weight loss %) according to this test of less than 20%, or in other embodiments less than 15, 14, 13, 12, 11, 10, 9, 8, 7, 6, 5, 4, 3, 2, 1, 0.5, or 0.1%. This is the test referenced in the claims.

Antibacterial activity. Clay bars that are the subject of the examples disclosed herein are evaluated for potential activity.

In vitro microbiological tests, specifically zone of inhibition test sand rapid agar plate assays, were conducted to determine the antibacterial efficacy of one aspect, the clay bar skin cleanser, of the present invention. The following are the methods incorporated, and the results therein obtained, from the analysis regarding antibacterial efficacy.

Preparation of bacterial culture. Staphylococcus aureus ATCC #6538 was used in this investigation since this organism is regarded as the representative skin bacteria. A uniform procedure was adopted to grow and process bacterial culture throughout this study. For each experiment, fresh bacterial cells were prepared by growing a single colony of bacteria in 20 ml of TSB at 37° C. After 18-20 hours of growth, bacteria were pelleted by centrifuging at 3000 rpm for 20 min at 4° C. The supernatant was discarded and the pellet was resuspended in 20 ml of PBS and centrifuged again, this step helps to remove cellular debris thereby minimizes variability in bacterial counts. Finally, the pellet was resuspended in PBS and the optical density was adjusted to 0.1 at 620 nm using a spectrophotometer (Spectrophotometer, Lambda 40, Parkin Elmer).

The Zone of inhibition test includes two parts. First, Seeded Trypticase Soy Agar (TSA) plates were used to perform ZOI test. A uniform system is used to seed 100 µl of the bacterial suspension with optical density (OD) adjusted to 0.1 at 620 nm. Using a positive displacement pipette, 100 µl of the bacterial suspension was inoculated on the TSA surface. Using a flamed metal spreader, bacterial suspension was uniformly distributed on the entire agar surface.

Next, there is the placement of the soap sample. Using sterile punch biopsy 6 mm size of clay and other bar samples were aseptically punched out and kept in 12 well plate. A pair of forceps dipped in ethanol and flamed and used to pick up the soap piece and placed on the marked area over the freshly seeded bacteria. Test was conducted on duplicate plates. Plates were incubated at 37° C. After 18-20 hours, plates were examined for the zone of inhibition, zone size was measured and plates were photographed for visual demo.

Rapid Agar Plate Assay (RAPA). RAPA includes three elements. RAPA is a surrogate assay developed to mimic forearm wash clinical cup scrub assay. In this assay, the TSA plate is used as a alternative substrate for forearm. The TSA plate is washed with the test product and after air-drying, a specific dose of bacteria applied on the washed agar surface and incubated. To calculate product efficacy, determine the number of bacteria that have grown. In other words, the lower the number of bacteria grown then the higher the product efficacy.

The first of those three elements in the RAPA procedure is the preparation of the bacterial inoculum. The bacterial culture is then prepared using the same procedure as mentioned above. However, in RAPA, only a countable number of bacteria are applied to make it a quantitative method. A uniform system was developed to seed 100 µl of a diluted bacterial suspension that will allow growth of 250-400 colony-forming units (cfu) of bacteria on a 100 mm TSA plate. To attain this, 0.1 OD bacterial suspension was further diluted in phosphate buffered saline (PBS) up to $10^{-6}$ in a 10-fold dilution manner. Bacterial challenge dose (100 µl) was derived from the dilution $10^{-4}$.

Next in the RAPA procedure is the washing of TSA plates with the test product and subsequent drying. TSA plates in triplicate were washed with running tap water and/or soap samples following the RAPA method developed in house. For purposes of the example disclosed herein, every effort was made to minimize inherent variability. Among other variables, temperature and flow rate of tap water were kept uniform. These steps deemed critical in product evaluation. Therefore, a standard water temperature and flow rate was used in this study. The water temperature was adjusted to 92-96° C. and water flow was adjusted to 100 ml/sec as measured by a graduated beaker. After washing with the test product, plates were air dried inside a Class II, Biohazard Hood in inverted position for 45 min.

Lastly, the agar surface of the TSA plate (net area 50.24 cm$^2$) is washed with the bar soap as is. For convenience, 2.54-3.2 cm (1-1.25 inch) piece of the bar was used. Agar surface was briefly rinsed under running tap water. Using gloved hand, bar soap piece was moistened in water and directly applied for 10 seconds, lathered for 40 seconds and was rinsed for 10 seconds. Plates were air dried by placing in inverted position inside a running Biohazard Hood for 45 min. The challenge dose of bacteria (100 µl) from $10^{-4}$ dilution was inoculated using a positive displacement pipette and uniformly dispersed using a sterile metal spreader. Plates were incubated at 37° C. for 18-24 hrs. Next day bacterial colonies on plates were counted and plates were then photographed.

Varimixer Results and Assessments.

Preparation observations. Occasional grainy material may be found in the final dough mixture. This may possibly be attributed to inefficiencies in the Varimixer. Analysis confirms that the grains are unbroken pieces of SCI and/or re-solidified wax. One possible means to eliminate the grains is by the extension of mixing times, especially the step in which the talc is being mixed in with the meltables. As for possibilities for removing wax, the wax re-solidifies when cold or room temperature liquids are added into the mixture. It is contemplated that this may be avoided by preheating the liquids in a hot water bath. Also, it was found that large concentrations of hydrophobics (e.g. >10% wax, fatty alcohol, etc.) resulted in an excessively sticky dough that impeded the collection of the finished dough mixture from the Varimixer.

Wax screening. In previous experimentation, a wax screening was conducted in the lab and results showed negligible differences amongst the finished samples. Those experiments also illustrated the difficulties in preparing samples with high melting point waxes (e.g. the polyethylene Asensa waxes).

White Orokerite (a mixture of ceresin and paraffin wax, manufactured by Strahl & Pitsch), synthetic beeswax, paraffin, microcrystalline, and ceresin wax are the waxes evaluated in this screening. As for the finished product, all of the formulations in this series produced very smooth and high gloss bars. Only sample H7 (8 wt. % ceresin wax) had noticeable grainy material throughout the bar. Striations were also noticed on the bars, as a result of the soap plodder/extruder.

Use-Up Rates Analysis.
Numerical Data for Wax Screening Use-Up Rate Analysis

| Sample | Initial Mass (g) | Post-10 Washes Mass (g) | Post-10 Washes Wt. % Loss | Post-20 Washes Mass (g) | Post-20 Washes Wt. % Loss | Post-30 Washes Mass (g) | Post-30 Washes Wt. % Loss |
|---|---|---|---|---|---|---|---|
| Control | 70.56 | 63.89 | 9.46 | 58.97 | 7.70 | 53.01 | 10.11 |
| H1 | 129.08 | 110.92 | 14.07 | 96.05 | 13.41 | 79.78 | 16.94 |
| H2 | 133.68 | 114.23 | 14.55 | 99.11 | 13.24 | 82.28 | 16.98 |
| H3 | 131.99 | 111.76 | 15.33 | 97.05 | 13.16 | 81.06 | 16.47 |
| H4 | 130.25 | 109.38 | 16.02 | 93.32 | 14.68 | 76.91 | 17.58 |
| H5 | 129.36 | 109.48 | 15.37 | 94.69 | 13.51 | 79.09 | 16.48 |
| H6 | 131.63 | 115.15 | 12.52 | 101.75 | 11.64 | 86.36 | 15.13 |
| H7 | 128.62 | 110.38 | 14.18 | 96.54 | 12.54 | 81.93 | 15.13 |

Overall Wt. % Loss for Wax Screening Use-Up Analysis:

| Sample | No. of Washes 10 | 20 | 30 | Description |
|---|---|---|---|---|
| Control | 9.46 | 16.43 | 24.88 | 4717-122, 85/15 soap re-pressed |
| H1 | 14.07 | 25.59 | 38.19 | White Ozokerite Wax, 4% |
| H2 | 14.55 | 25.86 | 38.45 | Synthetic Beeswax, 4% |
| H3 | 15.33 | 26.47 | 38.58 | Paraffin Wax, 4% |
| H4 | 16.02 | 28.35 | 40.95 | Microcrystalline Wax, 4% |
| H5 | 15.37 | 26.8 | 38.86 | Ceresin Wax, 4% |
| H6 | 12.52 | 22.7 | 34.39 | Ceresin Wax, 6% |
| H7 | 14.18 | 24.94 | 36.3 | Ceresin Wax, 8% |

After the use-up rate analysis, all of the clay-bars displayed approximately the same extent of cracking when fully dried.

All of the clay-bar used in the examples disclosed herein have similar cracking patterns that are likely to originate from the extrusion process. This cracking is slightly less noticeable in the 6% and 8% ceresine wax prototypes (H6 and H7) in comparison with the other samples. Also, some slough is formed during the evaluation and some mass is lost through this process. The amount of slough formed seemed to be identical amongst the clay bar samples. The control did not display any cracking and had negligible slough formation during the use-up analysis.

These results illustrate that varying the wax type does not affect the use-up rates of the bar. All of the 4% wax samples had around 38-40% weight loss after 30 washes, in contrast to the <25% weight loss for the 85/15 control bar soap. The 6% and 8% wax samples display a slight improvement over the 4% prototypes, at 34.4% and 36.3% weight loss, respectively. This observation is a surprise, as one would expect the 8% wax sample to have a lower use-up rate. However, during the washing assessment, it was found that the 8% wax sample had in homogenous lumps throughout the bar due to incomplete mixing of the batch. It is likely that the wax was not fully incorporated throughout the bar and therefore the results of this prototype cannot be taken reliably.

In one preferred aspect of the present invention, a clay-bar prepared without wax (E4, contains 3% stearyl alcohol instead of wax) has a 28.6% weight loss compared to 18.0% weight loss of the control after 20 washes.

In yet another preferred aspect of the present invention (H6, 6% ceresin wax) the clay bar has a 22.70% weight loss compared to 16.43% for the control after 20 washes.

It must be noted that the control sample for the use-up rate analysis of E4 was Irish Spring™ Aloe bar soap whereas the current control is an 85/15 soap bar.

Slough Formation Assessment. Here, the 4% wax bars were relatively similar in performance, except for the White Ozokerite wax based bar.

The increase in wax concentration also saw a correlating decrease in slough. The 8% wax sample performed better than the 6% wax sample in this test, in contrast to the reverse result in the use-up analysis. Slough Assessment Results from Wax Screening:

| Formulation No. | Initial Mass (g) | Description of Slough | Final Mass (g) | Weight % Loss |
|---|---|---|---|---|
| Control | 70.17 | AMT: 3-Consistency homogenous & viscous fluid | 67.99 | 3.11 |
| H1 | 127.67 | AMT: 3-Consistency homogenous & viscous fluid | 118.43 | 7.24 |
| H2 | 132.75 | AMT: 7-Consistency of smaller particle oatmeal | 114.96 | 13.40 |
| H3 | 131.12 | AMT: 9-Consistency of large particle oatmeal (chunky) | 116.04 | 11.50 |
| H4 | 128.1 | AMT: 10-Consistency of large particle oatmeal (chunky) | 110.67 | 13.61 |
| H5 | 128.41 | AMT: 10-Consistency of large particle oatmeal (chunky) | 113.99 | 11.23 |
| H6 | 131.78 | AMT: 4-Consistency homogenous & viscous fluid | 123.02 | 6.65 |
| H7 | 127.45 | AMT: 4-Consistency homogenous & viscous fluid | 121.23 | 4.88 |

Fatty Alcohol Screening.

From previous experimentation, it was found that behenyl alcohol had too high of a melting point for it to be feasibly produced in the lab, where hand contact with the dough mixture is required during the last molding step. As for the stearyl alcohol, the data shows that stearyl alcohol imparts very similar properties to the clay bar as wax—it does not have a strong impact on the lather profile, enhances the water resistance significantly, and hardens the bar. In this experiment, behenyl and stearyl alcohols are reassessed in the formulations using the new Varimixer method.

With the Varimixer, the behenyl alcohol did not present an issue during the preparation process. The bars that were prepared had the same striated surface, like the previous bars. The clay bar 'chip' was also much more homogenous, due to lengthened mixing times with more rigorous mixing speeds. In addition, the stearyl alcohol based samples are noticeably smoother than the other clay bars.

Numerical Data for Fatty Alcohol Screening Use-Up Rate Analysis

| | | Post 10 Washes | | Post 20 Washes | |
|---|---|---|---|---|---|
| Sample | Initial Weight | Weight (g) | % Wt. Loss | Weight (g) | % Wt. Loss |
| Control | 69.79 | 63.72 | 8.69 | 56.98 | 10.57 |
| H6 | 131.85 | 115.64 | 12.29 | 97.51 | 15.68 |
| I1 | 116.23 | 99.78 | 14.16 | 83.70 | 16.12 |
| I2 | 132.58 | 115.42 | 12.95 | 98.05 | 15.04 |
| I3 | 133.58 | 115.13 | 13.81 | 96.77 | 15.95 |
| (XXXV) | 127.32 | 112.43 | 11.69 | 95.83 | 14.77 |

Overall Wt. % Loss for Fatty Alcohol Screening Use-Up Analysis

| | No. of Washes | | |
|---|---|---|---|
| Sample | 10 | 20 | Description |
| Control | 8.69 | 18.35 | 85/15 soap re-pressed |
| H6 | 12.29 | 26.04 | Ceresine Wax, 6% |
| I1 | 14.16 | 27.99 | Behenyl Alcohol, 4% |
| I2 | 12.95 | 26.04 | Stearyl Alcohol, 4% |
| I3 | 13.81 | 27.55 | Behenyl Alcohol, 2%; Ceresine Wax 2% |
| XXXV | 11.69 | 24.73 | |

From the use-up rate analysis both the stearyl and behenyl alcohol based samples have about the same wear rate as the wax based sample, at 26.04, 27.99, and 26.04 wt. % loss after 20 washes, respectively. The differentiating factor of these bars comes in with the cracking issues. Stearyl alcohol based samples showed very minimal signs of cracking after use, versus that of the behenyl alcohol and wax based samples which showed more noticeable cracking along the striations. Aside from the cracking issue, however, these results reaffirm those that were concluded in previous experimentation. It is likely that any highly hydrophobic substance that is not easily solubilized by the surfactant system can impart to the same degree of water resistance to the clay bar.

Slough formation Assessment. The 4% stearyl alcohol based sample (I2) has the lowest weight percent loss at only 14.2% compared to 18.0% for the behenyl alcohol based sample.

It was found that the behenyl alcohol based samples had deeper fissures along the striations on their sloughing side after the slough formation test. This indicates more water penetration of the bars, specifically through the striations produced during the extruding process. It is theorized that this is more prevalent in the behenyl alcohol based samples due to the fact that behenyl alcohol has a higher melting point of 65-72° C. (149-162° F.), which is well above the temperature of the heating jacket 43-54° C. (~110-130° F.) in the extruder. This may lead to striations that are more easily penetrated by water. Stearyl alcohol, on the other hand, has a melting point of 56-59° C. (133-138° F.). The fact that the stearyl alcohol based samples did not crack along the striations and had a smoother surface supports this explanation.

Slough Assessment Results from Fatty Alcohol Screening

| Formulation No. | Initial Mass (g) | Description of Slough | Final Mass (g) | % Wt. Loss |
|---|---|---|---|---|
| I1 | 115.97 | white mush | 95.04 | 18.0 |
| I2 | 132.78 | white mush | 113.93 | 14.2 |
| I3 | 132.21 | white mush | 109.39 | 17.3 |
| XXXV | 125.53 | white mush | 106.75 | 15.0 |
| Control | 69.89 | opaque, viscous gel | 67.11 | 4.0 |

Polawax™ Evaluation.

In this experiment, a different type of hydrophobic ingredient is assessed in the clay bar formula. Polawax™, an emulsifying wax (higher fatty alcohols) from Croda, is evaluated in the clay bar as the binding agent. The bars created in this experiment were smooth, although the striated pattern on the surface of the bars is still present.

Use-up rates analysis in Polawax™ evaluation. It was calculated that there was an 8.38-11.48 wt. % loss difference between the Polawax™ samples and the control. For the wax screening experiment, the numbers come out to 6.27 wt. % loss difference for H6 (6% ceresin wax) and ~9.5 wt. % loss difference for the 4% wax samples evaluated. Thus, Polawax™ is about equivalent to the other waxes in terms of improving the wear properties of the clay bar.

Numerical Data for Use-Up Rate Analysis of Polawax™ Samples

|  |  | | Post 10 Washes | | Post 20 Washes | |
|---|---|---|---|---|---|---|
| Sample | Trial | Initial Mass (g) | Mass (g) | Wt. % Loss | Mass (g) | Wt. % Loss |
| Control | 1 | 73.536 | 66.151 | 10.04 | 59.040 | 10.750 |
| Control | 2 | 73.650 | 65.991 | 10.40 | 58.785 | 10.920 |
| J1 | 1 | 129.893 | 111.360 | 14.27 | 93.105 | 16.393 |
| J1 | 2 | 130.417 | 111.270 | 14.68 | 93.469 | 15.998 |
| J2 | 1 | 128.896 | 107.303 | 16.75 | 87.909 | 18.074 |
| J2 | 2 | 129.443 | 108.406 | 16.25 | 89.239 | 17.681 |
| J3 | 1 | 135.382 | 115.145 | 14.95 | 97.108 | 15.665 |
| J3 | 2 | 134.040 | 114.072 | 14.90 | 95.981 | 15.859 |

Overall Wt. % Loss for Use-Up Analysis of Polawax™ Samples

|  | No. of Washes | | |
|---|---|---|---|
| Sample | 10 | 20 | Description |
| Control | 10.22 | 19.95 | 4728-259, 85/15 soap re-pressed |
| J1 | 14.48 | 28.33 | Polawax, 4% |
| J2 | 16.50 | 31.43 | Polawax 2%, SCI 5% |
| J3 | 14.93 | 28.33 | Polawax 2%, SLES 14% |

Slough Formation Assessment. In this experiment, we found that the performance of Polawax™ is not on par with the other waxes in terms of sloughing. Following the same method as the use-up rates analysis, the weight percent loss difference is used to compare Polawax™ with the other waxes evaluated. For the Polawax™ samples, the numbers ranges from 12.2-15.6 wt % loss difference. As for the wax screening samples, H6 had only a 3.54 wt, % loss difference and a range of 8.1-10.5 wt % loss difference for the other 4% wax samples.

It is theorized that the above observations could be attributed to Polawax™ properties as an emulsifying wax, traditionally used in lotions to help emulsify the highly hydrophobic emollients. Since the slough test subjects the bar (and consequently the Polawax™) to being submerged in water for a long period, it could be that a local emulsion is created where the bar is submerged. This would potentially aid the water in degrading the bar and increasing slough since the Polawax™ is no longer acting as a binding agent when it is emulsified.

Slough Formation Assessment in Polawax™ Evaluation.

Slough Assessment Results for Polawax Samples

| Sample | Trial | Initial Mass (g) | Description of Slough | Final Mass (g) | % Wt. Loss | Average |
|---|---|---|---|---|---|---|
| Control | 1 | 74.454 | opaque, viscous gel | 69.731 | 6.3 | 6.4 |
| Control | 2 | 73.725 | opaque, viscous gel | 69.011 | 6.4 |  |
| J1 | 1 | 130.963 | white mush | 107.212 | 18.1 | 18.6 |
| J1 | 2 | 129.816 | white mush | 105.039 | 19.1 |  |
| J2 | 1 | 129.036 | white mush | 100.807 | 21.9 | 22.0 |
| J2 | 2 | 129.637 | white mush | 100.971 | 22.1 |  |
| J3 | 1 | 134.27 | white mush | 105.916 | 21.1 | 21.4 |
| J3 | 2 | 135.472 | white mush | 106.037 | 21.7 |  |

Surfactant Reduction Trials.

Previous experimentation has shown that the composition and concentration of surfactants is the most influential aspect in the performance properties of the clay bar. In the following examples, surfactant levels are reduced in an attempt to improve wear and slough rates. Hydrophobic ingredient concentration is also increased to create a tertiary binding system of hydrogenated soybean oil, ceresin wax, and stearyl alcohol.

Use-Up Rates Analysis in Surfactant Reduction Trials.
Numerical Data for Use-Up Rate Analysis of Surfactant Reduction Trials

|  |  |  | Post-10 Washes | | Post-20 Washes | |
|---|---|---|---|---|---|---|
| Sample | Trial | Initial Mass (g) | Mass (g) | Wt. % Loss | Mass (g) | Wt. % Loss |
| Control | 1 | 71.67 | 65.36 | 8.81 | 59.25 | 9.35 |
| H6 | 1 | 130.80 | 112.90 | 13.69 | 97.58 | 13.56 |
| I2 | 1 | 130.63 | 113.06 | 13.45 | 96.32 | 14.81 |
| K1 | 1 | 128.01 | 110.72 | 13.51 | 94.78 | 14.39 |
|  | 2 | 128.25 | 111.01 | 13.45 | 95.06 | 14.36 |
| K2 | 1 | 127.35 | 109.85 | 13.74 | 94.28 | 14.17 |
|  | 2 | 127.52 | 110.26 | 13.54 | 94.70 | 14.11 |
| K3 | 1 | 128.33 | 112.02 | 12.71 | 96.97 | 13.44 |
|  | 2 | 128.57 | 111.62 | 13.19 | 96.77 | 13.30 |

Overall Wt. % Loss for Use-Up Analysis of Surfactant Reduction Trials

|  | No. of Washes | | |
|---|---|---|---|
| Sample | 10 | 20 | Description |
| Control | 8.81 | 17.33 | 85/15 soap |
| H6 | 13.69 | 25.40 | 6% Ceresin Wax |
| I2 | 13.45 | 26.27 | 4% Stearyl Alcohol |
| K1 | 13.51 | 25.96 | 4% Ceresin Wax, 4% Stearyl Alcohol |
|  | 13.45 | 25.88 |  |
| K2 | 13.74 | 25.97 | 4% Ceresin Wax, 4% Stearyl Alcohol,- |
|  | 13.54 | 25.74 | 3% Surfactants |
| K3 | 12.71 | 24.44 | 4% Ceresin Wax, 4% Stearyl Alcohol,- |
|  | 13.19 | 24.73 | 5% Surfactants |

From the above results, it can be noted that the numbers are very close to one another, bringing into question statistical significance. The trend, however, can be seen that sample 12 (4% stearyl alcohol) is has the highest use-up, which is expected since previous studies showed it being inferior to H6 (6% ceresin wax). The increase in hydrophobics and decrease in surfactants, on the contrary did not show much of an improvement over the wear rate of the samples.

The overall surfactant concentration was decreased by reducing SCI and CMEA along with the SLES. From prior experimentation, it has been observed that CMEA barely affects the wear rates and SCI to a small extent. None of the bars in this example had same cracking issues that were apparent on some of the bars from other examples. This observation could mean that the extruding process may lead to significant impacts on the clay bar's performance.

Slough formation assessment in surfactant reduction trials. The results from this assessment illustrate that despite the reduced surfactant levels, the clay bars still had relatively the same amount of slough formation. Sample 12 demonstrated the least amount of water resistance, with 17.86 wt % loss. The sloughing side of the bars also did not show the same fissure-like cracks along the striations, thus indicating the billets were extruded well. This further supports the initial hypothesis that the extrusion process may make an impact on the performance of the clay bar.

Slough Assessment Results from Surfactant Reduction Trials

| Sample | Trial | Initial Mass (g) | Observations | Final Mass (g) | Wt. % Loss | Average Wt. % Loss |
|---|---|---|---|---|---|---|
| Control | 1 | 71.49 | opaque viscous gel | 69.57 | 2.68 | 2.68 |
| H6 | 1 | 132.20 | significantly less slough than the other clay bars | 111.89 | 15.36 | 15.36 |
| I2 | 1 | 128.44 | white mush | 105.50 | 17.86 | 17.86 |
| K1 | 1 | 128.05 | white mush | 107.07 | 16.39 | 16.75 |
|  | 2 | 129.00 | white mush | 106.94 | 17.10 |  |
| K2 | 1 | 126.74 | white mush | 106.63 | 15.87 | 15.82 |
|  | 2 | 127.25 | white mush | 107.17 | 15.77 |  |
| K3 | 1 | 128.60 | white mush | 107.27 | 16.59 | 16.35 |
|  | 2 | 128.61 | while mush | 107.89 | 16.11 |  |

Panel Tests.

Panel evaluations were conducted on the clay bars formed in these Varimixer examples. The bars were evaluated against an 85/15 control bar soap as well as several other clay bars. Panels of 14-15 volunteers were given the test bar and control bar to use and compare various attributes immediately and 10 minutes after washing.

First Panel Test:
List of Samples Tested in 1$^{st}$ Panel Test.

| Sample ID | Description |
|---|---|
| Control | 85/15 control bar soap |
| H5 | 17% surfactants, 4% HSO, 4% ceresin wax |
| H6 | 17% surfactants, 4% HSO, 6% ceresin wax; |
| (XXXV) | 17% surfactants, 6% HSO |
| E3 | 15% surfactants, 2.5% HSO, 2.5% PKO, 3% stearyl alcohol |

The table below illustrates first panel results regarding lather preference of tested compounds.

| Sample | Panelists preferring Control | Panelists Preferring Example |
|---|---|---|
| H5 | 5 | 10 |
| H6 | 8 | 7 |
| XXXV | 7 | 8 |
| E3 | 6 | 5 |

The tables below illustrate first panel results regarding skin feel preference results of tested compounds.

|  | Immediate | | After 10 Minutes | |
|---|---|---|---|---|
| Sample | Panelists preferring Control | Panelists Preferring Example | Panelists preferring Control | Panelists Preferring Example |
| H5 | 7 | 6 | 8 | 6 |
| H6 | 7 | 5 | 6 | 5 |
| XXXV | 8 | 7 | 8 | 6 |
| E3 | 3 | 8 | 6 | 4 |

Second Panel Test:
In the second panel test, a Polawax™ based bar was tested alongside a PKO based bar.

List of Samples Tested in 2$^{nd}$ Panel Test.

| Sample ID | Description |
|---|---|
| Control | 85/15 control bar soap |
| J1 | 17% surfactants, 4% HSO, 4% Polawax ™ |
| E2 | 17% surfactants, 2.5% HSO, 4.5% PKO |

The tables below illustrate second panel results regarding lather preference

| Sample | Panelists preferring Control | Panelists Preferring Example |
|---|---|---|
| E2 | 4 | 9 |
| J1 | 7 | 7 |

The table below illustrates skin feel results for 4% Polawax™ bar. The number is the average rating from panelists on a scale of 1 to 10 rated 10 minutes after washing.

|  | Control | J1 |
|---|---|---|
| Feels clean | 7.77 | 7.92 |
| Feels moisturized | 5.31 | 5.77 |
| Feels soft | 5.38 | 6.15 |
| Feels smooth | 5.62 | 6.15 |
| Feels dry | 4.23 | 3.31 |
| Looks dry | 2.77 | 2.92 |
| Feels draggy | 2.15 | 2.00 |

The table below illustrates skin feel results for 4.5% PKO bar. The number is the average rating from panelists on a scale of 1 to 10 rated 10 minutes after washing.

|  | Control | E2 |
|---|---|---|
| Feels clean | about 8 | about 8 |
| Feels moisturized | about 5.4 | about 6.3 |
| Feels soft | about 5.9 | about 6.3 |
| Feels smooth | about 6 | about 6.3 |
| Feels dry | about 3.5 | about 2.9 |
| Looks dry | about 2.9 | about 2.1 |
| Feels draggy | about 2 | about 1.5 |

In Vitro Antibacterial Efficacy Study.

Clay bar soaps in this example were tested by both the zone of inhibition ("ZOI") test and by RAPA. The ZOI test demonstrated increased antibacterial efficacy when measured against the control bar of soap. The clay bar used was formula E2.

Zone of Inhibition Testing.

FIG. 1A demonstrates that the clay bar of this example produced an 18-20 mm ZOI when assayed using the zone of inhibition test. FIG. 1B demonstrates that there is no clear ZOI observed with a plain 85/15 bar soap when assayed using the zone of inhibition test. The ZOI test was repeated and compared with some other leading brands including Irish Spring™ and Lever2000™. Figures IC and ID demonstrate that upon repeated ZOI testing that the clay bar again evidenced large and clear zone of inhibition when measured against other test products. Clay bar (I), Lever 2000 soap (II), Irish Spring soap (III).

Rapid Agar Plate Assessment (RAPA).

Figure 2B:
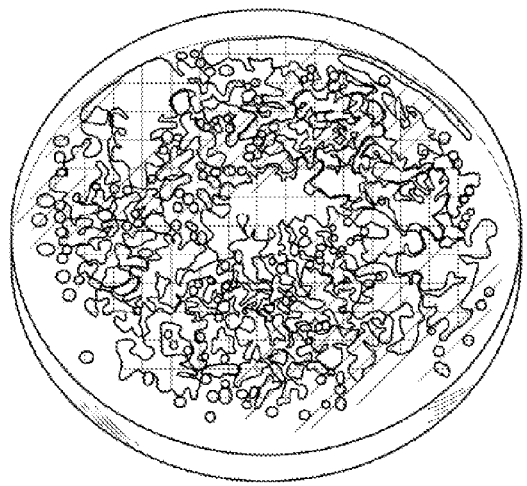
Figure 2C:
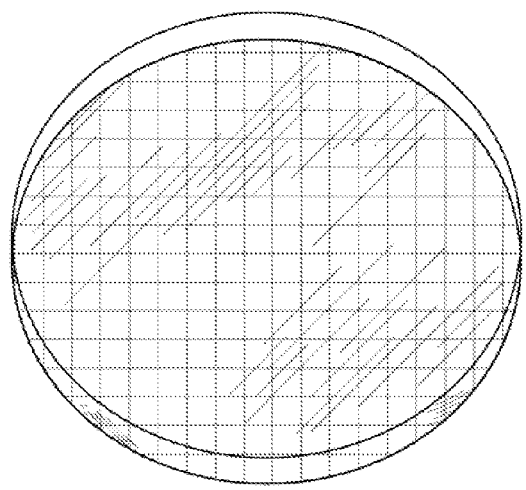

The following examples demonstrate the clay bar's residual efficacy. RAPA testing was conducted on the clay bar prototype and compared with other test products known in the marketplace: Lever2000™, and Irish Spring™. FIGS. 2A-2C (2A is water control, 2B is Irish Spring Soap, and 3C is clay bar soap) illustrate the efficacy of the clay bar when tested against other soap products. The clay bars of this example illustrate bacterial growth prevention on the agar plate in a significantly improved manner over those products that it was tested against. Plates washed with the clay bar of this example showed complete inhibition of the growth of bacteria. This inhibition may indicate that residual deposition efficacy of ingredients in the agar plates causing bacterial inhibition.

The RAPA testing demonstrates that the clay bar soap of this example does indeed deposit some ingredients on the agar during washing that appeared to inhibit the growth of *S. aureus*. Based on these results, it is reasonable to conclude that the clay bars of this example would likely have residual antibacterial activity on skin, even after a user has rinsed off. It is clear from these in vitro studies that this clay bar formula has antibacterial activity. It is possible that this mechanism of antibacterial action is due either to the clay itself or the high level of SLES and/or other additives in the formula.

Because the clay bars of this example, and other relevant examples disclosed herein, incorporate a SLES surfactant, and not the traditional soap mix, this presents an improvement over the art wherein the clay bars of the examples disclosed herein have the ability to deliver antibacterial efficacy without having any chemical antibacterial active. It is possible that the clay bar of the examples disclosed herein may also deliver other skin health benefits such as anti-acne and exfoliation.

In the claims, the amounts of all materials are selected so that the total is 100%.

What is claimed is:

1. A cleansing bar comprising:
   clay, wherein a total amount of clay is present in an amount that is greater than any other material in the cleansing bar, and the total amount of clay is at least 40 weight % of the cleansing bar, wherein the clay is at least one clay chosen from kaolin, kaolinite, dickite, halloysite, nacrite, smectite, montmorillonite, nontronite, illite, bentonite, attapulgite, palygorskite, sepiolite, hormite, pyrophyllite, chlorite, and aluminosilicates, and wherein the clay excludes talc,
   a cleanser consisting essentially of a surfactant, wherein the surfactant is present in an amount of 5 to 25 weight % of the cleansing bar,
   at least one of palm kernel oil and hydrogenated soybean oil, and
   at least one binder chosen from paraffin, polymethylene wax, and polyethylene wax, present in an amount to structure the cleansing bar into a bar and present in an amount of at least 1 weight % of the cleansing bar,
   wherein either soap is not present in the cleansing bar or soap is present in an amount of less than 0.5 weight % of the cleansing bar.

2. The cleansing bar of claim 1, wherein the total amount of clay is at least 50 weight % of the cleansing bar.

3. The cleansing bar of claim 1, wherein the surfactant comprises an anionic surfactant.

4. The cleansing bar of claim 1, wherein the surfactant comprises at least one surfactant chosen from sodium cocoyl methyl isethionate and sodium laureth sulfate.

5. The cleansing bar of claim 1, wherein the binder comprises polyethylene wax.

6. The cleansing bar of claim 1, wherein the binder is present in an amount of at least 2 weight % of the cleansing bar.

7. The cleansing bar of claim 1, wherein the cleansing bar comprises: 40 to 60 weight % clay, 12 to 20 weight % cleanser consisting essentially of a surfactant, 4 to 5 weight % hydrogenated soybean oil, and 2 to 3 weight % palm kernel oil.

8. The cleansing bar of claim 1, wherein the cleansing bar comprises 40 to 50 weight % clay, 10 to 15 weight % cleanser consisting essentially of a surfactant, and 10 to 15 weight % binder.

9. The cleansing bar of claim 1 further comprising glycerin.

10. The cleansing bar of claim 1, wherein the cleansing bar has a slough (weight loss %) less than 20%.

11. A method of making the cleansing bar of claim 1 comprising mixing the clay with the at least one binder before mixing in the cleanser consisting essentially of a surfactant.

12. A method of removing bacteria from skin comprising washing skin with a cleansing bar comprising:
    clay, wherein a total amount of clay is present in an amount that is greater than any other material in the cleansing bar, and the total amount of clay is at least 40 weight % of the cleansing bar, wherein the clay is at least one clay chosen from kaolin, kaolinite, dickite, halloysite, nacrite, smectite, montmorillonite, nontronite, illite, bentonite, attapulgite, palygorskite, sepiolite, hormite, pyrophyllite, chlorite, and aluminosilicates, and wherein the clay excludes talc,
    a cleanser consisting essentially of a surfactant, wherein the surfactant is present in an amount of 5 to 25 weight % of the cleansing bar,
    at least one of palm kernel oil and hydrogenated soybean oil, and
    at least one binder chosen from paraffin, polymethylene wax, and polyethylene wax, present in an amount to structure the cleansing bar into a bar and present in an amount of at least 1 weight % of the cleansing bar,
    wherein either soap is not present in the cleansing bar or soap is present in an amount of less than 0.5 weight % of the cleansing bar.

13. A method of inhibiting bacterial growth on skin comprising washing skin with a cleansing bar comprising:

clay, wherein a total amount of clay is present in an amount that is greater than any other material in the cleansing bar, and the total amount of clay is at least 40 weight % of the cleansing bar, wherein the clay is at least one clay chosen from kaolin, kaolinite, dickite, halloysite, nacrite, smectite, montmorillonite, nontronite, illite, bentonite, attapulgite, palygorskite, sepiolite, hormite, pyrophyllite, chlorite, and aluminosilicates, and wherein the clay excludes talc, a cleanser consisting essentially of a surfactant, wherein the surfactant is present in an amount of 5 to 25 weight % of the cleansing bar, at least one of palm kernel oil and hydrogenated soybean oil, and at least one binder chosen from paraffin, polymethylene wax, and polyethylene wax, present in an amount to structure the cleansing bar into a bar and present in an amount of at least 1 weight % of the cleansing bar, wherein either soap is not present in the cleansing bar or soap is present in an amount of less than 0.5 weight % of the cleansing bar.

14. The cleansing bar of claim 4 further comprising at least one surfactant chosen from cocamidopropyl betaine and cocomonoethanolamide.

15. The cleansing bar of claim 1, wherein the cleansing bar contains less than 8 weight % of fatty material based on the weight of the cleansing bar.

* * * * *